US012029484B2

United States Patent
Chen et al.

(10) Patent No.: US 12,029,484 B2
(45) Date of Patent: Jul. 9, 2024

(54) METHOD AND DEVICE OF DETERMINING DISTANCE AND HEIGHT BASED ON A PLURALITY OF SENSORS

(71) Applicants: NUCTECH COMPANY LIMITED, Beijing (CN); Tsinghua University, Beijing (CN)

(72) Inventors: Zhiqiang Chen, Beijing (CN); Yuanjing Li, Beijing (CN); Xianghao Wu, Beijing (CN); Haitao Zhang, Beijing (CN); Jundi Dai, Beijing (CN); Shaozhi Zhao, Beijing (CN); Guocheng An, Beijing (CN)

(73) Assignees: NUCTECH COMPANY LIMITED, Beijing (CN); Tsinghua University, Beijing (CN)

(*) Notice: Subject to any disclaimer, the term of this patent is extended or adjusted under 35 U.S.C. 154(b) by 632 days.

(21) Appl. No.: 17/286,573

(22) PCT Filed: Feb. 24, 2021

(86) PCT No.: PCT/CN2021/077571
§ 371 (c)(1),
(2) Date: Apr. 19, 2021

(87) PCT Pub. No.: WO2021/185031
PCT Pub. Date: Sep. 23, 2021

(65) Prior Publication Data
US 2022/0304574 A1    Sep. 29, 2022

(30) Foreign Application Priority Data
Mar. 16, 2020 (CN) .......................... 202010184163.5

(51) Int. Cl.
*A61B 3/11* (2006.01)
*A61B 3/14* (2006.01)

(52) U.S. Cl.
CPC ................. *A61B 3/112* (2013.01); *A61B 3/14* (2013.01)

(58) Field of Classification Search
CPC ......... A61B 3/112; A61B 3/14; A61B 3/0083; A61B 5/107; A61B 5/1072; A61B 5/1075;
(Continued)

(56) References Cited

U.S. PATENT DOCUMENTS

| 2002/0118114 A1 | 8/2002 | Ohba et al. |
| 2008/0179506 A1 | 7/2008 | Pirkl |

(Continued)

FOREIGN PATENT DOCUMENTS

| CN | 1629874 A | 6/2005 |
| CN | 1871994 A | 12/2006 |

(Continued)

OTHER PUBLICATIONS

Chinese Office Action for CN Application No. 202010184163.5 dated Jan. 27, 2022 (10 pages).

(Continued)

*Primary Examiner* — Collin X Beatty
(74) *Attorney, Agent, or Firm* — Merchant & Gould P.C.

(57) ABSTRACT

The present disclosure provides a method of determining a distance and a height, including: measuring, a first distance, a second distance and a third distance from the security inspection device to the tested person as well as measuring a first height, a second height and a third height of the tested person; determining, a relationship between the first distance and a minimum distance threshold as well as a maximum distance threshold, a relationship between the second distance and the minimum distance threshold as well as the maximum distance threshold, and a relationship between the third distance and the minimum distance threshold as well as (Continued)

the maximum distance threshold; determining, a final distance from the security inspection device to the tested person and a final height of the tested person; and performing a pixel conversion and a size conversion on the pupil image of the tested person.

12 Claims, 13 Drawing Sheets

(58) Field of Classification Search
CPC .......... G01B 21/02; G01V 8/10; G06F 18/00; G06Q 50/26
See application file for complete search history.

(56) References Cited

U.S. PATENT DOCUMENTS

| | | |
|---|---|---|
| 2013/0006068 A1 | 1/2013 | Gemer et al. |
| 2013/0170754 A1 | 7/2013 | Tsukizawa et al. |
| 2014/0268047 A1* | 9/2014 | Hirsh ..................... A61B 3/112 351/246 |
| 2017/0049373 A1* | 2/2017 | Jahnke ................. A61B 5/4088 |

FOREIGN PATENT DOCUMENTS

| | | |
|---|---|---|
| CN | 101190120 A | 6/2008 |
| CN | 101363722 A | 2/2009 |
| CN | 103186765 A | 7/2013 |
| CN | 104586386 A | 5/2015 |
| CN | 105704479 A | 6/2016 |
| CN | 108278467 A | 7/2018 |
| CN | 108374964 A | 8/2018 |
| CN | 109118636 A | 1/2019 |
| CN | 110013217 A | 7/2019 |
| CN | 110151184 A | 8/2019 |
| CN | 110393504 A | 11/2019 |
| CN | 209746151 U | 12/2019 |
| JP | 2001184483 A | 7/2001 |
| JP | 2002250605 A | 9/2002 |
| JP | 2004191083 A | 7/2004 |
| JP | 2006130325 A | 5/2006 |
| JP | 2007322212 A | 12/2007 |
| JP | 2020027465 A | 2/2020 |
| WO | WO-2017031331 A1 * | 2/2017 ........... A61B 3/0025 |

OTHER PUBLICATIONS

PCT International Search Report for CN Publication No. PCT/CN2021/077571 dated May 7, 2021 (3 pages).

* cited by examiner

METHOD AND DEVICE OF DETERMINING DISTANCE AND HEIGHT BASED ON A PLURALITY OF SENSORS

CROSS REFERENCE TO RELATED APPLICATION(S)

This application is a Section 371 National Stage Application of International Application No. PCT/CN2021/077571, filed on Feb. 24, 2021, which claims priority to Chinese patent Application No. CN 202010184163.5, filed on Mar. 16, 2020, the content of which are incorporated herein by reference in their entirety.

TECHNICAL FIELD

The present disclosure relates to a field of security inspection, and in particular to a method of determining a distance and a height based on a plurality of sensors, an electronic apparatus, and a computer-readable storage medium.

BACKGROUND

For a long time, in drug investigation, conventional test methods to check whether suspects have taken drugs include tests of urine, blood or saliva. However, these tests include many links such as sampling under supervision and often consume a lot of time, manpower and material resources, and test results are prone to false negatives, false positives, etc. due to interference. In addition, there are many kinds of drugs. Using urine test paper to check one by one may increase the use of urine test paper and increase costs, which is not suitable for extensive check. In addition, in recent years, some drug addicts have adopted special methods to neutralize drug metabolism in their bodies, which makes routine urine tests ineffective. Investigators may only use accurate test methods such as gas chromatography, gas chromatography-mass spectrometry, etc. which may take 2 to 3 days and cost high.

In order to solve these obvious drawbacks and many problems in the tests of drug addicts, there is a need to provide a safe and simple method of unconsciously collecting a pupil image of a person and analyzing the pupil image to determine whether the person takes drugs.

To align a user's face from a long distance, collect an eye image, segment a pupil image and calculate a size of the pupil, it is necessary to determine a distance from the user to the security inspection device and a height of the user.

At present, a method of estimating a pupil size from a long distance based on a video image processing is still immature, especially a distance measurement is not accurate, especially when heights of tested persons (1.5 meters to 2.1 meters) fluctuate greatly. Therefore, how to accurately determine the height of the tested person and the distance between the tested person and the security inspection device is a technical problem that needs to be solved.

SUMMARY

The present disclosure provides a method of determining a distance and a height by using a plurality of sensors so as to determine whether a tested person takes drugs or not based on a pupil image of the tested person, including: measuring, by respectively using a first sensor, a second sensor and a third sensor of the plurality of sensors arranged on a security inspection device, a first distance, a second distance and a third distance from the security inspection device to the tested person as well as measuring a first height, a second height and a third height of the tested person; determining, by using a first determination unit, a relationship between the first distance and a minimum distance threshold as well as a maximum distance threshold, a relationship between the second distance and the minimum distance threshold as well as the maximum distance threshold, and a relationship between the third distance and the minimum distance threshold as well as the maximum distance threshold; determining, by using a second determination unit, a final distance from the security inspection device to the tested person and a final height of the tested person, based on the relationships; and performing a pixel conversion and a size conversion on the pupil image of the tested person based on the final distance and the final height, so as to determine whether the tested person takes drugs or not.

According to a first aspect, the determining a final distance from the security inspection device to the tested person and a final height of the tested person, based on the relationships may include: determining the first distance as the final distance from the security inspection device to the tested person and determining the first height as the final height of the tested person, in response to determining that the second distance is less than the minimum distance threshold and the third distance is less than the minimum distance threshold, regardless of the relationship between the first distance and the minimum distance threshold as well as the maximum distance threshold.

According to the first aspect, the determining a final distance from the security inspection device to the tested person and a final height of the tested person, based on the relationships may include:

in response to determining that the second distance is less than the minimum distance threshold, and that the third distance is greater than or equal to the minimum distance threshold and less than or equal to the maximum distance threshold,
    determining the third distance as the final distance from the security inspection device to the tested person and determining the third height as the final height of the tested person, in response to determining that the first distance is less than the minimum distance threshold or greater than the maximum distance threshold; or
    determining whether an absolute value of a difference between the first distance and the third distance is less than a predetermined person-to-person distance or not, in response to determining that the first distance is greater than or equal to the minimum distance threshold and less than or equal to the maximum distance threshold,
        determining the first distance as the final distance from the security inspection device to the tested person and determining the first height as the final height of the tested person, in response to determining that the absolute value of the difference between the first distance and the third distance is less than the predetermined person-to-person distance; and
        determining a smaller distance of the first distance and the third distance as the final distance from the security inspection device to the tested person and determining a height associated with the smaller distance as the final height of the tested person, in response to determining that the absolute value of the difference between the first distance and the third distance is greater than or equal to the predetermined person-to-person distance.

According to the first aspect, the determining a final distance from the security inspection device to the tested person and a final height of the tested person, based on the relationships may include:

in response to determining that the second distance is less than the minimum distance threshold and that the third distance is greater than the maximum distance threshold,
determining the third distance as the final distance from the security inspection device to the tested person and determining the third height as the final height of the tested person, in response to determining that the first distance is less than the minimum distance threshold; or
determining a smaller distance of the first distance and the third distance as the final distance from the security inspection device to the tested person and determining a height associated with the smaller distance as the final height of the tested person, in response to determining that the first distance is greater than the maximum distance threshold; or
determining the first distance as the final distance from the security inspection device to the tested person and determining the first height as the final height of the tested person, in response to determining that the first distance is greater than or equal to the minimum distance threshold and less than or equal to the maximum distance threshold.

According to the first aspect, the determining a final distance from the security inspection device to the tested person and a final height of the tested person, based on the relationships may include:

in response to determining that the second distance is greater than the minimum distance threshold and less than the maximum distance threshold, and that the third distance is less than the maximum distance threshold,
determining the second distance as the final distance from the security inspection device to the tested person and determining the second height as the final height of the tested person, in response to determining that the first distance is less than the minimum distance threshold or greater than the maximum distance threshold; or
determining whether an absolute value of a difference between the first distance and the second distance is less than a predetermined person-to-person distance or not, in response to determining that the first distance is greater than the minimum distance threshold and less than the maximum distance threshold,
determining the first distance as the final distance from the security inspection device to the tested person and determining the first height as the final height of the tested person, in response to determining that the absolute value of the difference between the first distance and the second distance is less than the predetermined person-to-person distance; and
determining a smaller distance of the first distance and the second distance as the final distance from the security inspection device to the tested person and determining a height associated with the smaller distance as the final height of the tested person, in response to determining that the absolute value of the difference between the first distance and the second distance is greater than or equal to the predetermined person-to-person distance.

According to the first aspect, the determining a final distance from the security inspection device to the tested person and a final height of the tested person, based on the relationships may include:

in response to determining that each of the second distance and the third distance is greater than or equal to the minimum distance threshold and less than or equal to the maximum distance threshold,
determining whether an absolute value of a difference between the second distance and the third distance is less than a predetermined person-to-person distance or not, in response to determining that the first distance is less than the minimum distance threshold or greater than the maximum distance threshold,
determining the second distance as the final distance from the security inspection device to the tested person and determining the second height as the final height of the tested person, in response to determining that the absolute value of the difference between the second distance and the third distance is less than the predetermined person-to-person distance; and
determining a smaller distance of the second distance and the third distance as the final distance from the security inspection device to the tested person and determining a height associated with the smaller distance as the final height of the tested person, in response to determining that the absolute value of the difference between the second distance and the third distance is greater than or equal to the predetermined person-to-person distance; or
determining whether an absolute value of a difference between the first distance and the second distance is less than a predetermined person-to-person distance or not, whether an absolute value of a difference between the first distance and the third distance is less than the predetermined person-to-person distance or not, and whether an absolute value of a difference between the second distance and the third distance is less than the predetermined person-to-person distance or not, in response to determining that the first distance is greater than or equal to the minimum distance threshold and less than or equal to the maximum distance threshold,
determining the first distance as the final distance from the security inspection device to the tested person and determining the first height as the final height of the tested person, in response to determining that each of the absolute value of the difference between the first distance and the second distance, the absolute value of the difference between the first distance and the third distance and the absolute value of the difference between the second distance and the third distance is less than the predetermined person-to-person distance; or
determining the third distance as the final distance from the security inspection device to the tested person and determining the third height as the final height of the tested person, in response to determining that the absolute value of the difference between the first distance and the second distance is greater than or equal to the predetermined person-to-person distance, and that each of the absolute value of the difference between the first distance and the third distance and the absolute value of the difference between the second distance and the third distance is less than the predetermined person-to-person distance; or
determining the first distance as the final distance from the security inspection device to the tested person and determining the first height as the final height of the tested person, in response to determining that each of the absolute value of the difference between the first distance and the second distance and the absolute value of the difference between the first distance and the third distance is less than the predetermined person-to-person distance, and that the absolute value of the difference between the second distance and the third distance is greater than or equal to the predetermined person-to-person distance; or determining the second distance as the final distance from the security inspection device to the tested person and determining the second height as the final height of the tested person, in response to determining that each of the absolute value of the difference between the first distance and the second distance and the absolute value of the difference between the second distance and the third distance is less than the predetermined person-to-person distance, and that the absolute value of the difference between the first distance and the third distance is greater than or equal to the predetermined person-to-person distance; or determining the third distance as the final distance from the security inspection device to the tested person and determining the third height as the final height of the tested person, in response to determining that the absolute value of the difference between the first distance and the second distance is less than the predetermined person-to-person distance, and that each of the absolute value of the difference between the first distance and the third distance and the absolute value of the difference between the second distance and the third distance is greater than or equal to the predetermined person-to-person distance; or determining the second distance as the final distance from the security inspection device to the tested person and determining the second height as the final height of the tested person, in response to determining that each of the absolute value of the difference between the first distance and the second distance and the absolute value of the difference between the first distance and the third distance is greater than or equal to the predetermined person-to-person distance, and that the absolute value of the difference between the second distance and the third distance is less than the predetermined person-to-person distance; or determining the first distance as the final distance from the security inspection device to the tested person and determining the first height as the final height of the tested person, in response to determining that each of the absolute value of the difference between the first distance and the second distance and the absolute value of the difference between the second distance and the third distance is greater than or equal to the predetermined person-to-person distance, and that the absolute value of the difference between the first distance and the third distance is less than the predetermined person-to-person distance; or determining the third distance as the final distance from the security inspection device to the tested person and determining the third height as the final height of the tested person, in response to determining that each of the absolute value of the difference between the first distance and the second distance, the absolute value of the difference between the first distance and the third distance and the absolute value of the difference between the second distance and the third distance is greater than or equal to the predetermined person-to-person distance.

According to the first aspect, the determining a final distance from the security inspection device to the tested person and a final height of the tested person, based on the relationships may include:

in response to determining that the second distance is greater than or equal to the minimum distance threshold and less than or equal to the maximum distance threshold, and that the third distance is greater than the maximum distance threshold,
 determining the third distance as the final distance from the security inspection device to the tested person and determining the third height as the final height of the tested person, in response to determining that the first distance is less than the minimum distance threshold or greater than the maximum distance threshold; or
 determining whether an absolute value of a difference between the first distance and the third distance is less than a predetermined person-to-person distance or not, in response to determining that the first distance is greater than or equal to the minimum distance threshold and less than or equal to the maximum distance threshold,
  determining the first distance as the final distance from the security inspection device to the tested person and determining the first height as the final height of the tested person, in response to determining that the absolute value of the difference between the first distance and the third distance is less than the predetermined person-to-person distance; or
  determining a smaller distance of the first distance and the third distance as the final distance from the security inspection device to the tested person and determining a height associated with the smaller distance as the final height of the tested person, in response to determining that the absolute value of the difference between the first distance and the third distance is greater than or equal to the predetermined person-to-person distance.

According to the first aspect, the determining a final distance from the security inspection device to the tested person and a final height of the tested person, based on the relationships may include:

in response to determining that the second distance is greater than the maximum distance threshold, and that the third distance is less than the minimum distance threshold,
 determining the third distance as the final distance from the security inspection device to the tested person and determining the third height as the final height of the tested person, in response to determining that the first distance is less than the minimum distance threshold; or
 determining a smaller distance of the first distance and the second distance as the final distance from the security inspection device to the tested person and determining a height associated with the smaller distance as the final height of the tested person, in response to determining that the first distance is greater than the maximum distance threshold; or
 determining the first distance as the final distance from the security inspection device to the tested person and determining the first height as the final height of the tested person, in response to determining that the first distance is greater than or equal to the minimum distance threshold and less than or equal to the maximum distance threshold.

According to the first aspect, the determining a final distance from the security inspection device to the tested person and a final height of the tested person, based on the relationships may include:

in response to determining that the second distance is less than the minimum distance threshold, and that the third distance is greater than or equal to the minimum distance threshold and less than or equal to the maximum distance threshold, determining the third distance as the final distance from the security inspection device to the tested person and determining the third height as the final height of the tested person, in response to determining that the first distance is less than the minimum distance threshold or greater than the maximum distance threshold; or determining whether an absolute value of a difference between the first distance and the third distance is less than a predetermined person-to-person distance or not, in response to determining that the first distance is greater than or equal to the minimum distance threshold and less than or equal to the maximum distance threshold, determining the first distance as the final distance from the security inspection device to the tested person and determining the first height as the final height of the tested person, in response to determining that the absolute value of the difference between the first distance and the third distance is less than the predetermined person-to-person distance; or determining a smaller distance of the first distance and the third distance as the final distance from the security inspection device to the tested person and determining a height associated with the smaller distance as the final height of the tested person, in response to determining that the absolute value of the difference between the first distance and the third distance is greater than or equal to the predetermined person-to-person distance.

According to the first aspect, the determining a final distance from the security inspection device to the tested person and a final height of the tested person, based on the relationships may include:

in response to determining that each of the second distance and the third distance is greater than the maximum distance threshold, determining a smaller distance of the second distance and the third distance as the final distance from the security inspection device to the tested person and determining a height associated with the smaller distance as the final height of the tested person, in response to determining that the first distance is less than the minimum distance threshold; or determining a smallest distance of the first distance, the second distance and the third distance as the final distance from the security inspection device to the tested person and determining a height associated with the smallest distance as the final height of the tested person, in response to determining that the first distance is greater than the maximum distance threshold; or determining the first distance as the final distance from the security inspection device to the tested person and determining the first height as the final height of the tested person, in response to determining that the first distance is greater than or equal to the minimum distance threshold and less than or equal to the maximum distance threshold.

According to a second aspect of the present disclosure, the present disclosure provides a device of determining a distance and a height by using a plurality of sensors so as to determine whether a tested person takes drugs or not based on a pupil image of the tested person, including: a first sensor, a second sensor and a third sensor of the plurality of sensors arranged on a security inspection device, configured to respectively measure a first distance, a second distance and a third distance from the security inspection device to the tested person as well as measure a first height, a second height and a third height of the tested person; a first determination unit, configured to determine a relationship between the first distance and a minimum distance threshold as well as a maximum distance threshold, a relationship between the second distance and the minimum distance threshold as well as the maximum distance threshold, and a relationship between the third distance and the minimum distance threshold as well as the maximum distance threshold; a second determination unit, configured to: determine a final distance from the security inspection device to the tested person and a final height of the tested person, based on the relationships; and perform a pixel conversion and a size conversion on the pupil image of the tested person based on the final distance and the final height, so as to determine whether the tested person takes drugs or not.

According to a third aspect of the present disclosure, there is provided an electronic apparatus, including: one or more processors; and a memory for storing one or more programs, wherein the one or more programs, when executed by the one or more processors, cause the one or more processors to perform the method described according to the first aspect.

According to a fourth aspect of the present disclosure, there is provided a computer-readable storage medium having executable instructions stored thereon that, when executed by a processor, cause the processor to perform the method described according to the first aspect.

Based on the above aspects provided in the present disclosure, error measurements of sensors caused by unfavorable factors such as sensor damage, overlapping of tested persons, deliberate occlusion, tall luggage in front, etc. may be effectively eliminated, and a distance closest to an actual distance from the security inspection device to the tested person and a height closest to an actual height of the tested person may be obtained, so that other processing (for example, a pixel conversion and a size conversion of the pupil image of the tested person) may be performed based on the accurate distance and height.

BRIEF DESCRIPTION OF THE DRAWINGS

The above-mentioned and other embodiments and features of the present disclosure will become more apparent by describing the embodiments of the present disclosure in detail with reference to the drawings.

DETAILED DESCRIPTION OF EMBODIMENTS

Figure 1:
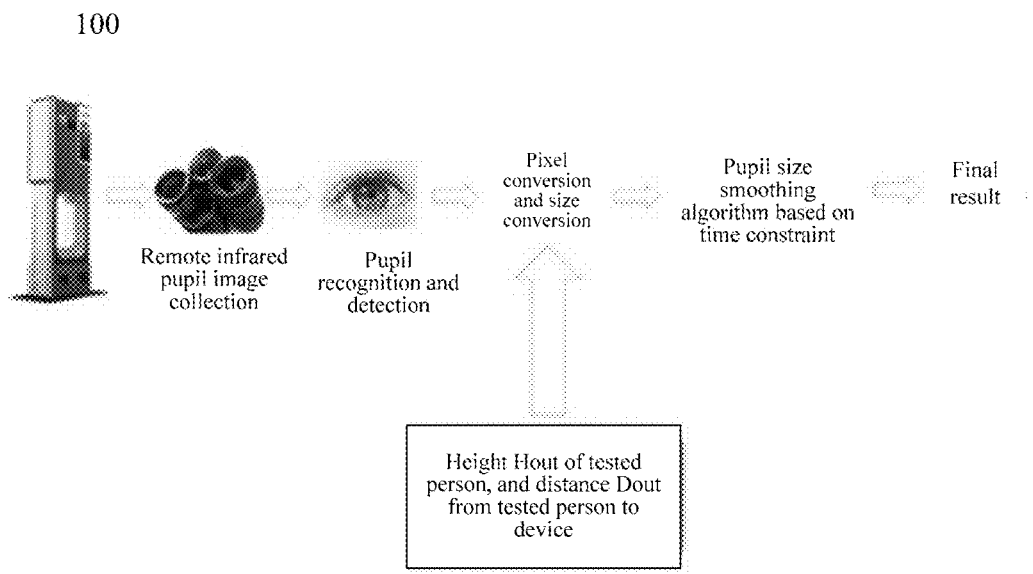
FIG. 1 schematically shows a system architecture of a method of determining a distance and a height based on a plurality of sensors according to an embodiment of the present disclosure.

Specific embodiments of the present disclosure will be described in detail below. It should be noted that the embodiments described here are only used for exemplification and are not used to limit the present disclosure. In the following description, a number of specific details are set forth in order to provide a thorough understanding of the present disclosure. However, it will be apparent to those ordinary skilled in the art that these specific details are not necessary to implement the present disclosure. In other examples, in order to avoid confusion with the present disclosure, well-known circuits, materials or methods are not specifically described.

Throughout the specification, references to "one embodiment," "an embodiment," "one example," or "an example" mean that a specific feature, structure, or characteristic described in conjunction with the embodiment or example is included in at least one embodiment of the present disclosure. Therefore, the phrases "in one embodiment", "in an embodiment", "one example" or "an example" appearing in various places throughout the specification do not necessarily refer to the same embodiment or example. Further, specific features, structures or characteristics may be combined in one or more embodiments or examples in any suitable combination and/or sub-combination.

It should be understood that when an element is referred to as being "coupled" or "connected" to another element, it may be directly coupled or connected to the other element, or there may be an intermediate element. However, when an element is described as being "directly coupled to" or "directly connected to" another element, no intermediate element is present.

The term "and/or" as used here includes any and all combinations of one or more related listed items.

It should be understood that a noun in a singular form corresponding to a term may include one or more things, unless the relevant context clearly indicates otherwise. As used herein, each of the phrases such as "A or B", "at least one of A and B", "at least one of A or B", "A, B or C", "at least one of A, B and C" and "at least one of A, B, or C" may include all possible combinations of items listed in the corresponding phase of the plurality of phrases. As used herein, terms such as "first" and "second" may be used to simply distinguish a corresponding component from another component and not to limit the components in other aspects (for example, importance or order).

As used herein, the term "module" may include a unit implemented in hardware, software, or firmware, and may be interchanged with other terms (for example, "logic", "logic block", "part" or "circuit"). A module may be a single integrated component adapted to perform one or more functions or a smallest unit or part of the single integrated component. For example, according to the embodiments, the module may be implemented in the form of an application specific integrated circuit (ASIC).

It should be understood that the various embodiments of the present disclosure and the terms used therein are not intended to limit the technical features set forth herein to specific embodiments, but include various changes, equivalents, or alternatives to the corresponding embodiments. Unless explicitly defined otherwise herein, all terms will give their broadest possible interpretations, including the meanings implied in the specification and those understood by those skilled in the art and/or defined in dictionaries, papers, etc.

In addition, those ordinary skilled in the art should understand that the drawings provided herein are for the illustrative purpose, and the drawings are not necessarily drawn to scale. For the description of the drawings, similar reference numerals may be used to refer to similar or related elements. The present disclosure will be exemplarily described below with reference to the drawings.

In order to solve the problem as explained in the BACKGROUND, the present disclosure provides a method of determining a distance and a height by using a plurality of sensors so as to determine whether a tested person takes drugs or not based on a pupil image of the tested person, including: measuring, by respectively using a first sensor, a second sensor and a third sensor of the plurality of sensors arranged on a security inspection device, a first distance, a second distance and a third distance from the security inspection device to the tested person as well as measuring a first height, a second height and a third height of the tested person; determining, by using a first determination unit, a relationship between the first distance and a minimum distance threshold as well as a maximum distance threshold, a relationship between the second distance and the minimum distance threshold as well as the maximum distance threshold, and a relationship between the third distance and the minimum distance threshold as well as the maximum distance threshold; determining, by using a second determination unit, a final distance from the security inspection device to the tested person and a final height of the tested person, based on the respective relationships; and performing a pixel conversion and a size conversion on the pupil image of the tested person based on the final distance and the final height, so as to determine whether the tested person takes drugs or not.

The present disclosure will be described below in detail with reference to the drawings and in conjunction with specific embodiments.

FIG. 1 schematically shows a system architecture of a method of determining a distance and a height based on a plurality of sensors according to an embodiment of the present disclosure. A system architecture 100 is a general architecture of detecting drug addicts, in which a remote infrared pupil image collection device of recognizing and detecting a pupil image of a tested person is provided on a security inspection device. After the pupil image of the tested person is obtained, a pixel conversion and a size conversion are performed on the pupil image based on a height of the tested person and a distance from the tested person to the security inspection device, and then it is determined whether the tested person is a drug addict based on the pupil image converted.

Therefore, a method and device of determining a distance and a height based on a plurality of sensors provided by the present disclosure are very important to determine whether the tested person takes drugs or not.

Figure 2:
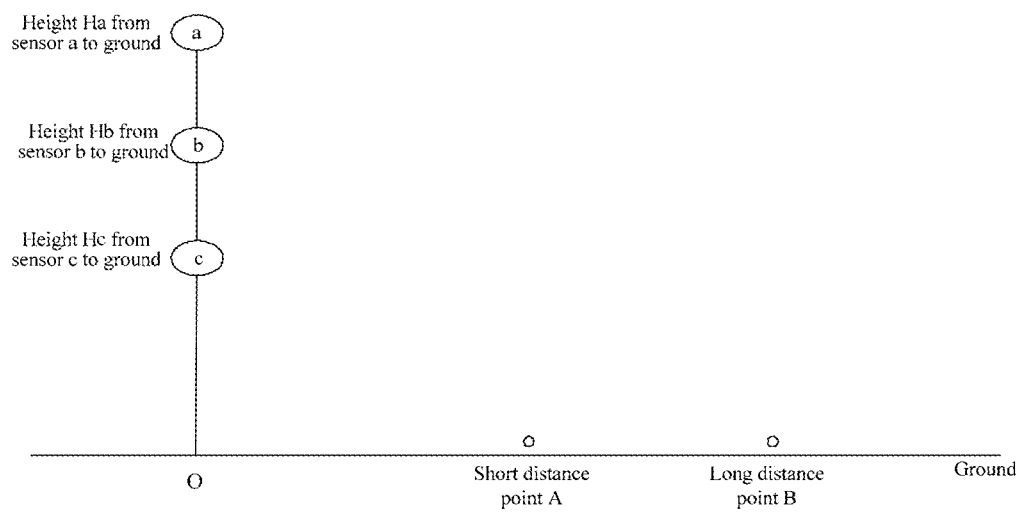
FIG. 2 schematically shows an exemplary arrangement of the plurality of sensors according to an embodiment of the present disclosure.

FIG. 2 schematically shows an exemplary arrangement of the plurality of sensors according to an embodiment of the present disclosure.

As shown in FIG. 2, a first sensor is arranged at a height a from the ground, a second sensor is arranged at a height b from the ground, and a third sensor is arranged at a height c from the ground.

Two reference points are set on the ground, namely a short distance point A and a long distance point B. The short distance point A is a minimum distance between the tested person and the sensors under the detection capability of the sensors, and the long distance point B is a maximum distance between the tested person and the sensors under the detection capability of the sensors.

In the present disclosure, a distance from the short distance point A to the security inspection device (point o in FIG. 2) is set as a minimum distance threshold, and a distance from the long distance point B to the security inspection device (point o in FIG. 2) is set as a maximum distance threshold.

In an exemplary embodiment, the first sensor, the second sensor and the third sensor may be same sensors or may be different sensors.

In the example where the first sensor, the second sensor and the third sensor are same sensors, for example, if the detection capability of the sensor is 300 cm to 400 cm, then the minimum distance threshold is 280 cm, and the maximum distance threshold is 420 cm.

During the security inspection, a flow of people usually passes through the security inspection device continuously. Therefore, there may be a situation where multiple tested persons pass through the security inspection device in close proximity to each other.

In view of this situation, to make a measurement result more accurate, a predetermined person-to-person distance is set in the present disclosure.

Preferably, the predetermined person-to-person distance may be set to 20 cm.

Figure 3:
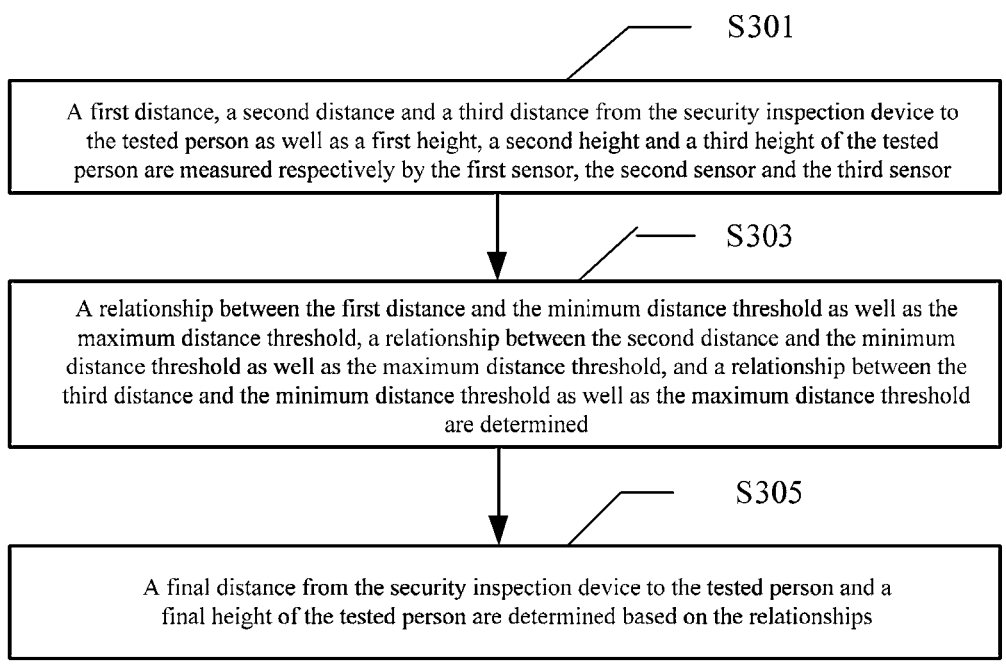
FIG. 3 schematically shows a flowchart of a method of determining a distance and a height based on a plurality of sensors according to an embodiment of the present disclosure.

FIG. 3 schematically shows a flowchart of a method of determining a distance and a height based on a plurality of sensors according to an embodiment of the present disclosure.

As shown in FIG. 3, the method includes following operations.

In operation S301, a first distance, a second distance and a third distance from the security inspection device to the tested person as well as a first height, a second height and a third height of the tested person are measured respectively by the first sensor, the second sensor and the third sensor.

In operation S303, a relationship between the first distance and the minimum distance threshold as well as the maximum distance threshold, a relationship between the second distance and the minimum distance threshold as well as the maximum distance threshold, and a relationship between the third distance and the minimum distance threshold as well as the maximum distance threshold are determined by using a first determination unit.

The first determining unit may be provided on the security inspection device.

Alternatively, the first determining unit may be provided in a processing device that is wired or wirelessly connected to the security inspection device.

In operation S305, a final distance from the security inspection device to the tested person and a final height of the tested person are determined by using a second determination unit, based on the relationships.

In the present disclosure, the final distance from the security inspection device to the tested person and the final height of the tested person may be defined as an optimal distance and an optimal height for the tested person determined based on the distances and heights respectively measured by the first sensor, the second sensor and the third sensor.

The second determination unit may be provided in the security inspection device.

Alternatively, the second determination unit may be provided in a processing device that is wired or wirelessly connected to the security inspection device.

The present disclosure takes into account unfavorable factors such as sensor failure, personnel overlap, deliberate occlusion, etc., and the distance closest to the actual distance from the security inspection device to the tested person as well as the height closest to the actual height of the tested person (that is, the final distance and the final height in the present disclosure) are determined based on the measurement results of the plurality of sensors (that is, the first sensor, the second sensor and the third sensor). The following will describe how to determine the final distance and the final height based on a relationship between the first distance and the minimum distance threshold as well as the maximum distance threshold, a relationship between the second distance and the minimum distance threshold as well as the maximum distance threshold, a relationship between the third distance and the minimum distance threshold as well as the maximum distance threshold, and the predetermined person-to-person distance.

Figure 4:
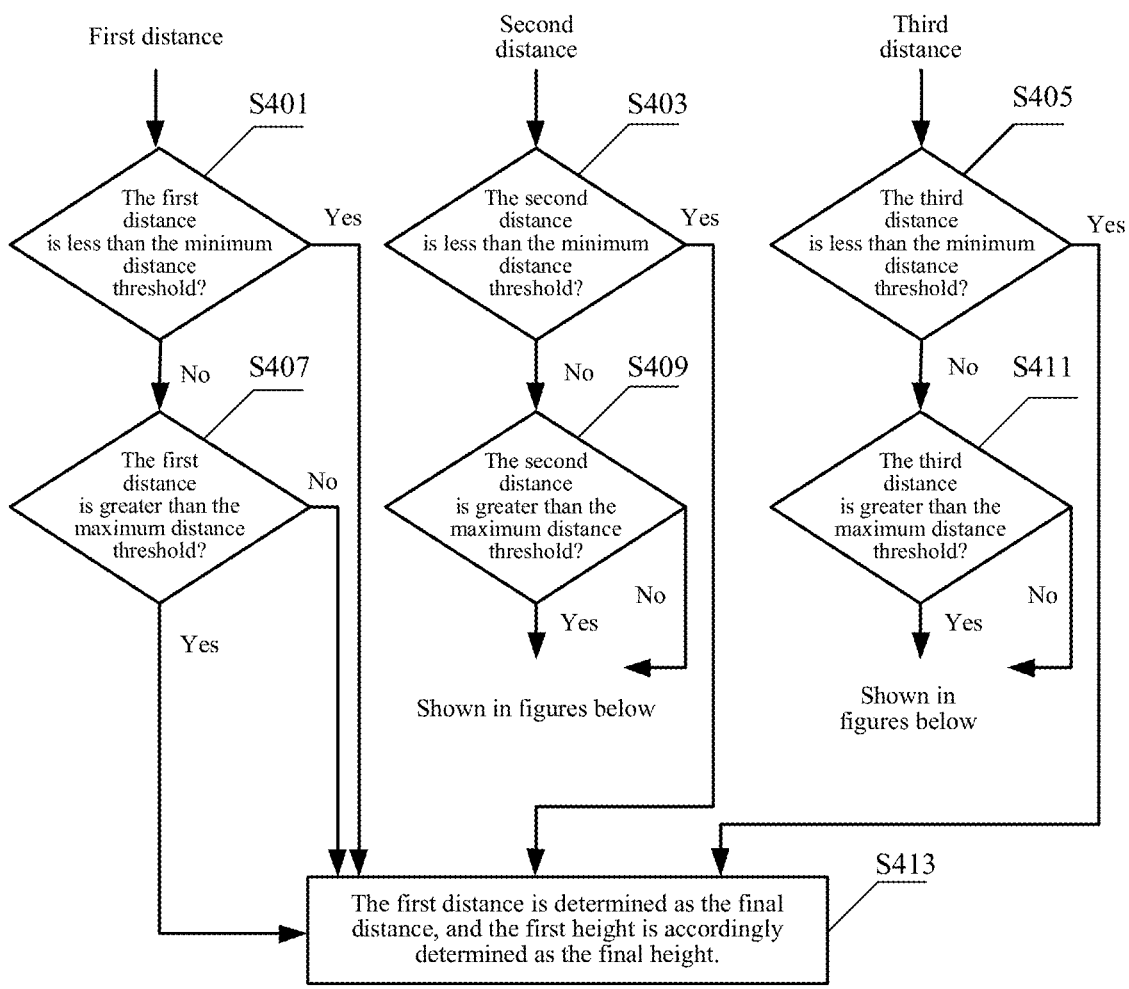
FIG. 4 schematically shows an exemplary flowchart of a first example of determining a final distance and a final height according to an embodiment of the present disclosure.

FIG. 4 schematically shows an exemplary flowchart of a first example of determining a final distance and a final height according to an embodiment of the present disclosure.

As shown in FIG. 4, the method includes following operations.

In operation S401, it is determined whether the first distance is less than the minimum distance threshold or not.

In operation S403, it is determined whether the second distance is less than the minimum distance threshold or not.

In operation S405, it is determined whether the third distance is less than the minimum distance threshold or not.

In operation S407, it is determined whether the first distance is greater than the maximum distance threshold or not.

In operation S409, it is determined whether the second distance is greater than the maximum distance threshold or not.

In operation S411, it is determined whether the third distance is greater than the maximum distance threshold or not.

In response to determining in operations S403 and S405 that the second distance is less than the minimum distance threshold and the third distance is less than the minimum distance threshold, the process proceeds to operation S413, regardless of the relationship between the first distance and the minimum distance threshold as well as the maximum distance threshold.

In operation S413, the first distance is determined as the final distance from the security inspection device to the tested person, and the first height is accordingly determined as the final height of the tested person.

In order to make the drawings clear, FIG. 4 only partially shows the example where the second distance is less than the minimum distance threshold and the third distance is less than the minimum distance threshold (regardless of the relationship between the first distance and the minimum distance threshold or the maximum distance threshold). Other examples will be described with reference to FIG. 5 to FIG. 12.

Figure 5:
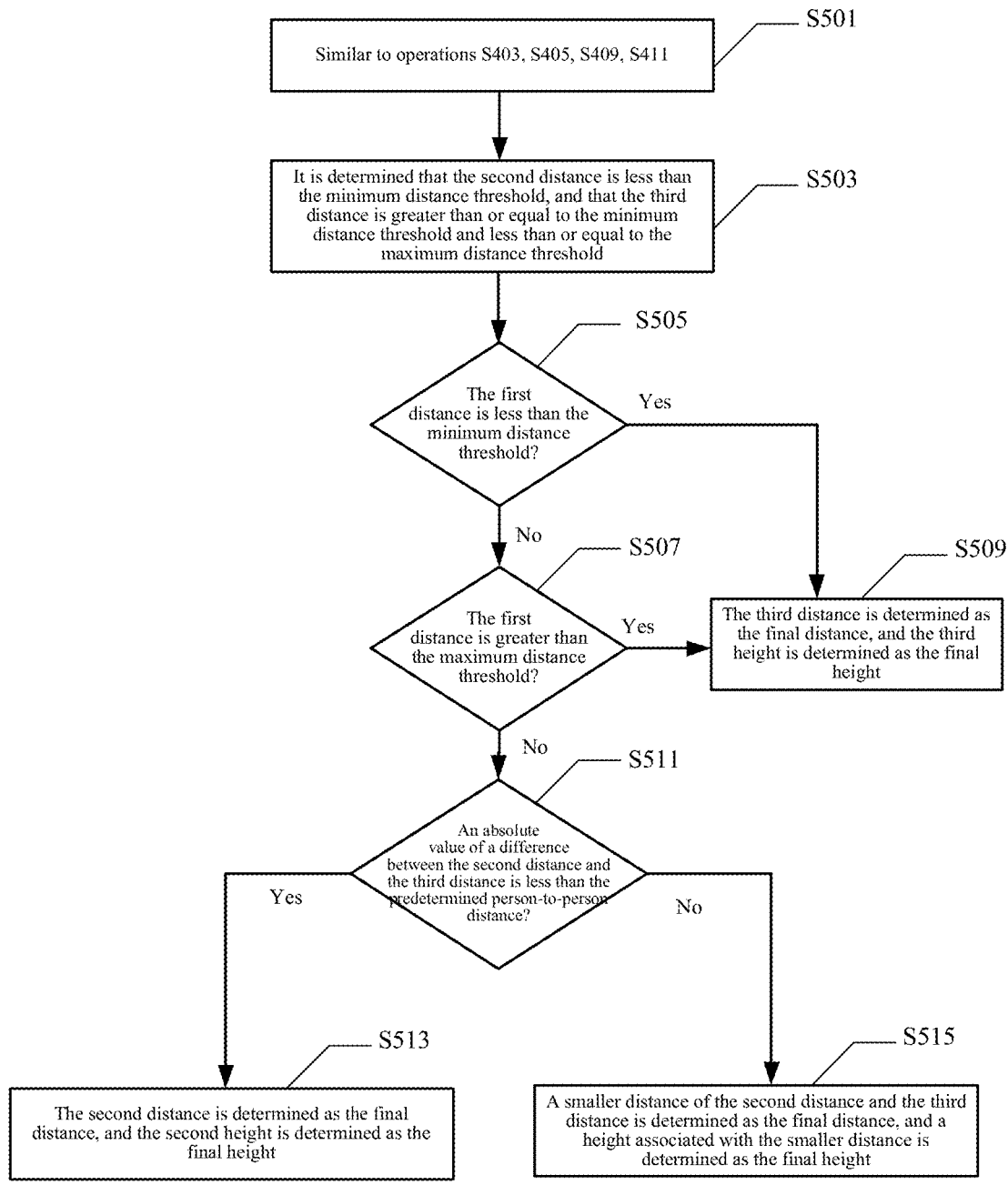
FIG. 5 schematically shows an exemplary flowchart of a second example of determining a final distance and a final height according to an embodiment of the present disclosure.

FIG. 5 schematically shows an exemplary flowchart of a second example of determining a final distance and a final height according to an embodiment of the present disclosure.

As shown in FIG. 5, the method includes following operations.

In operation S501, operations similar to operations S403, S405, S409 and S411 in FIG. 4 are performed.

In operation S503, it is determined that the second distance is less than the minimum distance threshold, and that the third distance is greater than or equal to the minimum distance threshold and less than or equal to the maximum distance threshold.

In operations S505 and S507, operations similar to operations S404 and S407 in FIG. 4 are performed to determine the relationship between the first distance and the minimum distance threshold as well as the maximum distance threshold.

In response to determining in operation S505 that the first distance is less than the minimum distance threshold, or determining in operation S507 that the first distance is greater than the maximum distance threshold, the process proceeds to operation S509.

In operation S509, the third distance is determined as the final distance, and the third height is determined as the final height.

In response to determining in operations S505 and S507 that the first distance is greater than or equal to the minimum distance threshold and less than or equal to the maximum distance threshold (a result of "No" is determined in operation S507), the process proceeds to operation S511.

In operation S511, it is determined whether an absolute value of a difference between the second distance and the third distance is less than the predetermined person-to-person distance or not.

In response to a result of "Yes" determined in operation S511, the process proceeds to operation S513.

In operation S513, the second distance is determined as the final distance, and the second height is determined as the final height.

In response to a result of "No" determined in operation S511, the process proceeds to operation S515.

In operation S515, a smaller distance of the second distance and the third distance (for example, the third distance) is determined as the final distance, and a height associated with the smaller distance (for example, the third height) is determined as the final height.

Figure 6:
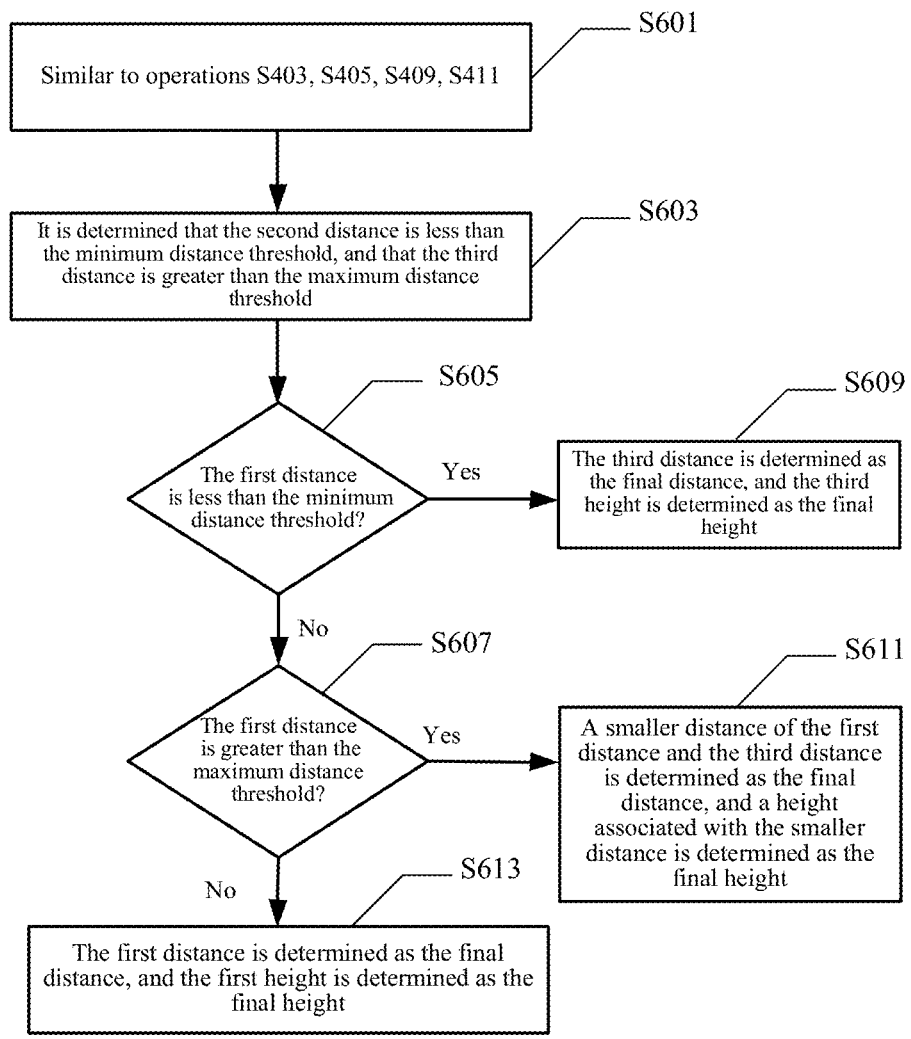
FIG. 6 schematically shows an exemplary flowchart of a third example of determining a final distance and a final height according to an embodiment of the present disclosure.

FIG. 6 schematically shows an exemplary flowchart of a third example of determining a final distance and a final height according to an embodiment of the present disclosure.

As shown in FIG. 6, the method includes following operations.

In operation S601, operations similar to operations S403, S405, S409 and S411 in FIG. 4 are performed.

In operation S603, it is determined that the second distance is less than the minimum distance threshold, and that the third distance is greater than the maximum distance threshold.

In operation S605, operations similar to operation S401 in FIG. 4 are performed.

In response to a result of "Yes" determined in operation S605, the process proceeds to operation S609.

In operation S609, the third distance is determined as the final distance, and the third height is determined as the final height.

In response to a result of "No" determined in operation S605, the process proceeds to operation S607.

In operation S607, operations similar to operation S407 in FIG. 4 are performed.

In response to a result of "Yes" determined in operation S607, a smaller distance of the first distance and the third distance (for example, the third distance) is determined as the final distance, and a height associated with the smaller distance (for example, the third height) is determined as the final height.

In response to a result of "No" determined in operation S607 (that is, the first distance is greater than or equal to the minimum distance threshold and less than or equal to the maximum distance threshold), the process proceeds to operation S613.

In operation S613, the first distance is determined as the final distance, and the first height is determined as the final height.

Figure 7:
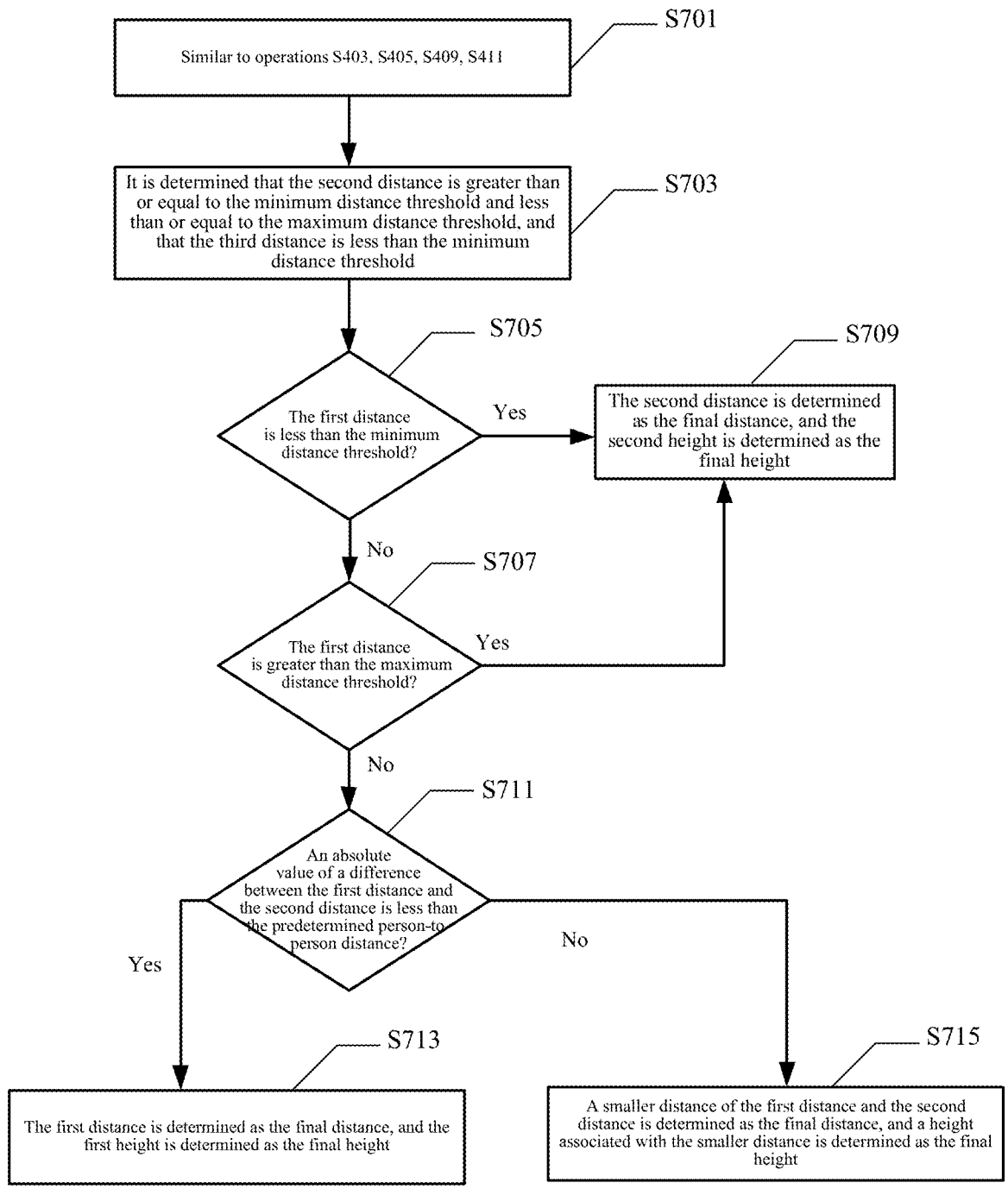
FIG. 7 schematically shows an exemplary flowchart of a fourth example of determining a final distance and a final height according to an embodiment of the present disclosure.

FIG. 7 schematically shows an exemplary flowchart of a fourth example of determining a final distance and a final height according to an embodiment of the present disclosure.

As shown in FIG. 7, the method includes following operations.

In operation S701, operations similar to operations S403, S405, S409 and S411 in FIG. 4 are performed.

In operation S703, it is determined that the second distance is greater than or equal to the minimum distance threshold and less than or equal to the maximum distance threshold, and that the third distance is less than the minimum distance threshold.

In operations S705 and S707, operations similar to operations S401 and S407 in FIG. 4 are performed.

In response to determining in operation S705 that the first distance is less than the minimum distance threshold, or determining in operation S707 that the first distance is greater than the maximum distance threshold, the process proceeds to operation S709.

In operation S709, the second distance is determined as the final distance, and the second height is determined as the final height.

In response to a result of "No" determined in operation S707 (that is, the first distance is greater than or equal to the minimum distance threshold and less than or equal to the maximum distance threshold), the process proceeds to operation S711.

In operation S711, it is determined whether an absolute value of a difference between the first distance and the second distance is less than the predetermined person-to-person distance or not.

In response to a result of "Yes" determined in operation S711, the process proceeds to operation S713.

In operation S713, the first distance is determined as the final distance, and the first height is determined as the final height.

In response to a result of "No" determined in operation S711, the process proceeds to operation S715.

In operation S715, a smaller distance of the first distance and the second distance is determined as the final distance, and a height associated with the smaller distance is determined as the final height.

Figure 8:
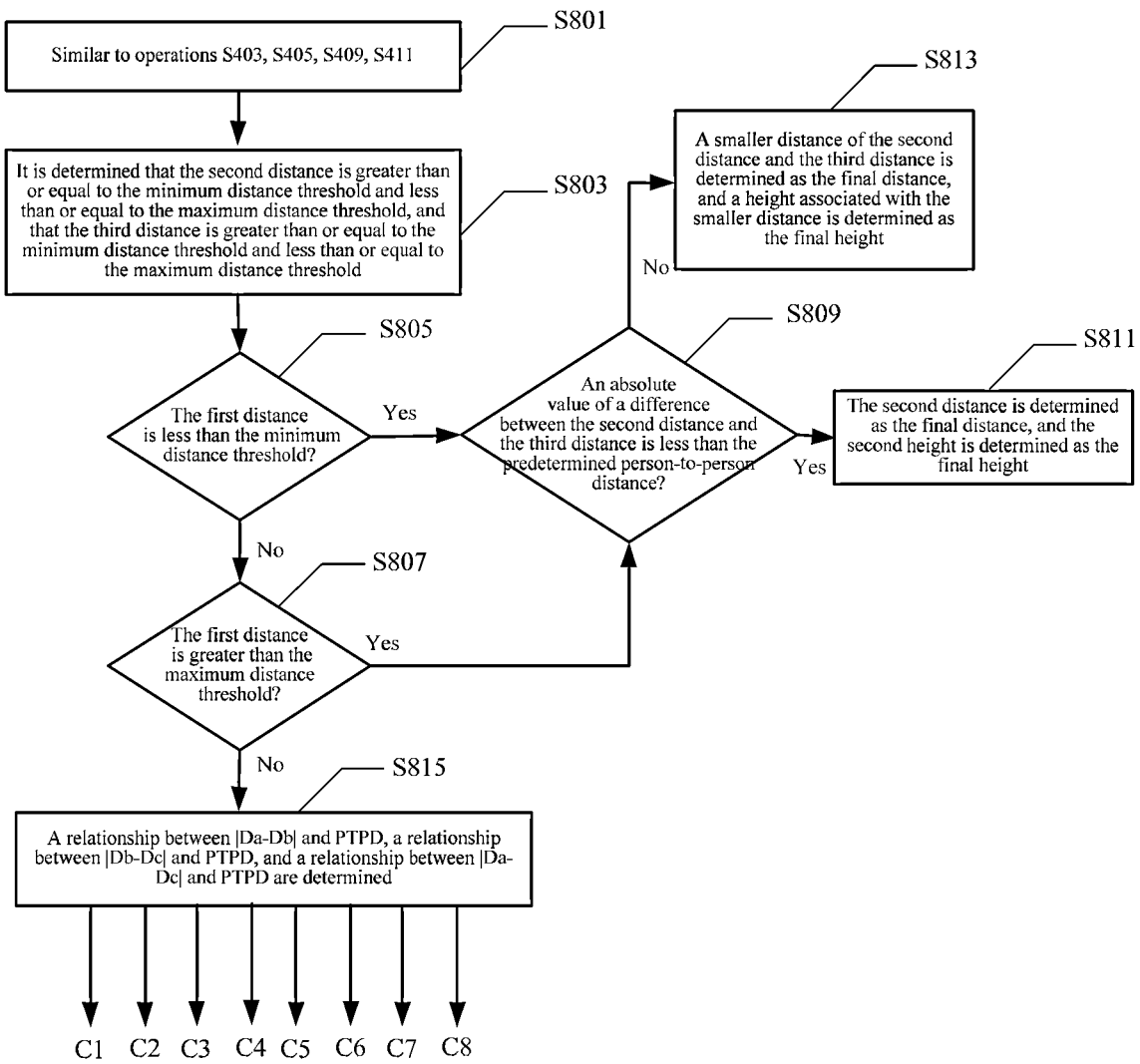
FIG. 8 schematically shows an exemplary flowchart of a fifth example of determining a final distance and a final height according to an embodiment of the present disclosure.

FIG. 8 schematically shows an exemplary flowchart of a fifth example of determining a final distance and a final height according to an embodiment of the present disclosure.

As shown in FIG. 8, the method includes following operations.

In operation S801, operations similar to operations S403, S405, S409 and S411 in FIG. 4 are performed.

In operation S803, it is determined that the second distance is greater than or equal to the minimum distance threshold and less than or equal to the maximum distance threshold, and that the third distance is greater than or equal to the minimum distance threshold and less than or equal to the maximum distance threshold.

In operations S805 and S807, operations similar to operations S401 and S407 in FIG. 4 are performed.

In response to determining in operation S805 that the first distance is less than the minimum distance threshold, or determining in operation S807 that the first distance is greater than the maximum distance threshold, the process proceeds to operation S809.

In operation S809, it is determined whether an absolute value of a difference between the second distance and the third distance is less than the predetermined person-to-person distance or not.

In response to a result of "Yes" determined in operation S809, the process proceeds to operation S811.

In operation S811, the second distance is determined as the final distance, and the second height is determined as the final height.

In response to a result of "No" determined in operation S809, the process proceeds to operation S813.

In operation S813, a smaller distance of the second distance and the third distance is determined as the final distance, and a height associated with the smaller distance is determined as the final height.

In response to a result of "No" determined in operation S807 (that is, the first distance is greater than or equal to the minimum distance threshold and less than or equal to the maximum distance threshold), the process proceeds to operation S815.

In operation S815, it is determined whether an absolute value of a difference between the second distance and the second distance is less than the predetermined person-to-person distance or not, whether an absolute value of a difference between the second distance and the third distance is less than the predetermined person-to-person distance or not, and whether an absolute value of a difference between the first distance and the third distance is less than the predetermined person-to-person distance or not.

Accordingly, eight different examples C1 to C8 may be obtained in S815. Each case example will be described in detail below.

In example C1, the absolute value of the difference between the first distance and the second distance is less than the predetermined person-to-person distance, the absolute value of the difference between the second distance and the third distance is less than the predetermined person-to-person distance, and the absolute value of the difference between the first distance and the third distance is less than the predetermined person-to-person distance (for ease of description, the first distance is denoted as Da, the second distance is denoted as Db, the third distance is denoted as Dc, and the predetermined person-to-person distance is denoted as PTPD). In this example, the first distance is determined as the final distance, and the first height is determined as the final height.

In example C2, it is determined $|Da-Db| \geq |Db-Dc| < PTPD$, $|Da-Dc| < PTPD$, then the third distance is determined as the final distance, and the third height is determined as the final height.

In example C3, it is determined $|Da-Db| < PTPD$, $|Db-Dc| \geq PTPD$, $|Da-Dc| < PTPD$, then the first distance is determined as the final distance, and the first height is determined as the final height.

In example C4, it is determined $|Da-Db| < PTPD$, $|Db-Dc| < PTPD$, $|Da-Dc| \geq PTPD$, then the second distance is determined as the final distance, and the second height is determined as the final height.

In example C5, it is determined $|Da-Db| < PTPD$, $|Db-Dc| \geq PTPD$, $|Da-Dc| \geq PTPD$, then the third distance is determined as the final distance, and the third height is determined as the final height.

In example C6, it is determined $|Da-Db| \geq PTPD$, $|Db-Dc| < PTPD$, $|Da-Dc| \geq PTPD$, then the second distance is determined as the final distance, and the second height is determined as the final height.

In example C7, it is determined $|Da-Db| \geq PTPD$, $|Db-Dc| \geq PTPD$, $|Da-Dc| < PTPD$, then the first distance is determined as the final distance, and the first height is determined as the final height.

In example C8, it is determined $|Da-Db| \geq PTPD$, $|Db-Dc| \geq PTPD$, $|Da-Dc| \geq PTPD$, then the third distance is determined as the final distance, and the third height is determined as the final height.

Figure 9:
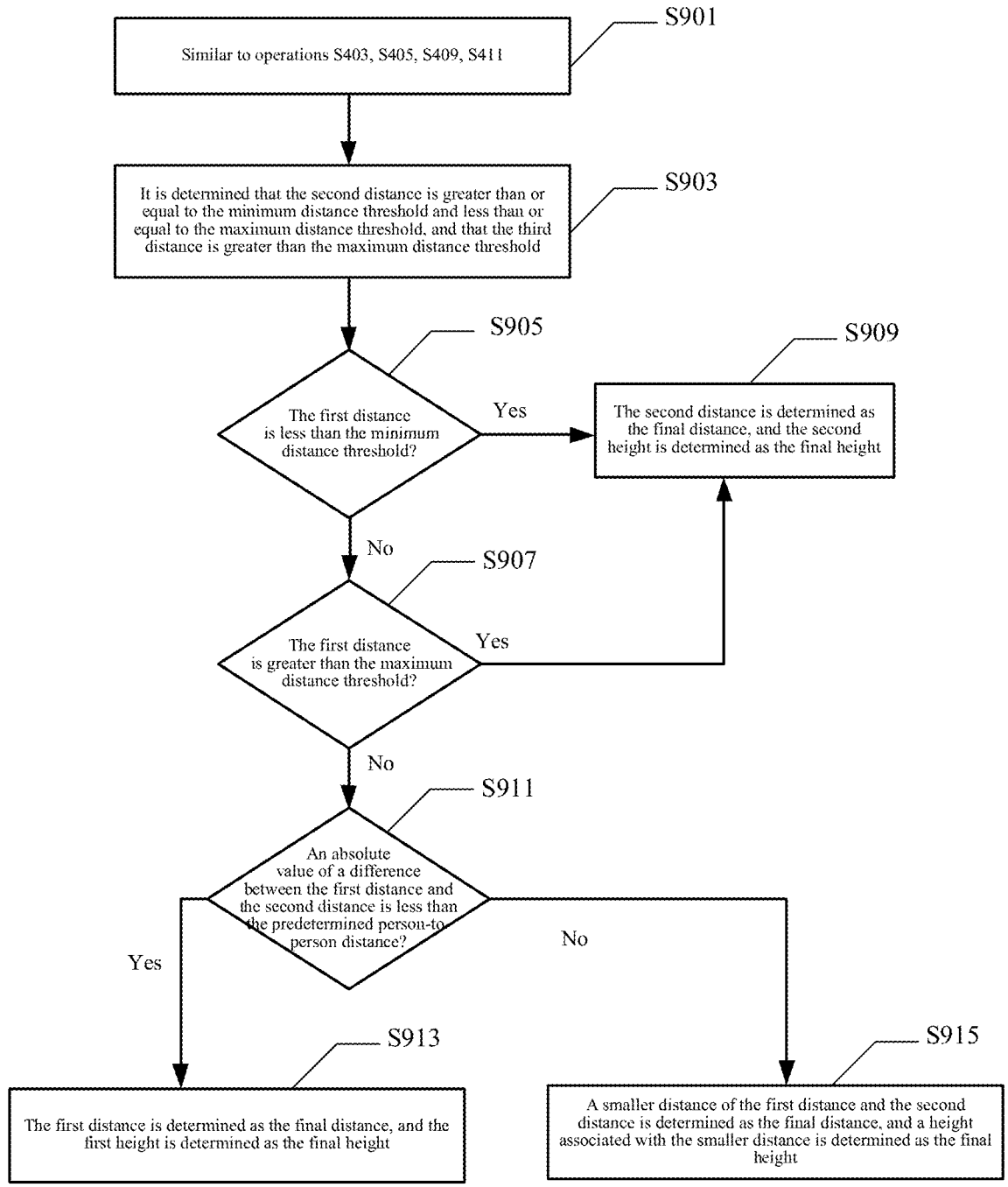
FIG. 9 schematically shows an exemplary flowchart of a sixth example of determining a final distance and a final height according to an embodiment of the present disclosure.

FIG. 9 schematically shows an exemplary flowchart of a sixth example of determining a final distance and a final height according to an embodiment of the present disclosure.

As shown in FIG. 9, the method includes following operations.

In operation S901, operations similar to operations S403, S405, S409 and S411 in FIG. 4 are performed.

In operation S903, it is determined that the second distance is greater than or equal to the minimum distance threshold and less than or equal to the maximum distance threshold, and that the third distance is greater than the maximum distance threshold.

In operations S905 and S907, operations similar to operations S401 and S407 in FIG. 4 are performed.

In response to determining in operation S905 that the first distance is less than the minimum distance threshold, or determining in operation S907 that the first distance is greater than the maximum distance threshold, the process proceeds to operation S909.

In operation S909, the second distance is determined as the final distance, and the second height is determined as the final height.

In response to a result of "No" determined in operation S907, the process proceeds to operation S911.

In operation S911, it is determined whether |Da−Db| is less than PTPD or not.

In response to determining that |Da−Db| is less than PTPD, the process proceeds to operation S913, in which the first distance is determined as the final distance, and the first height is determined as the final height.

In response to determining that |Da−Db| is greater than or equal to PTPD, the process proceeds to operation S915, in which a smaller distance of the first distance and the second distance is determined as the final distance, and a height associated with the smaller distance is determined as the final height.

Figure 10:
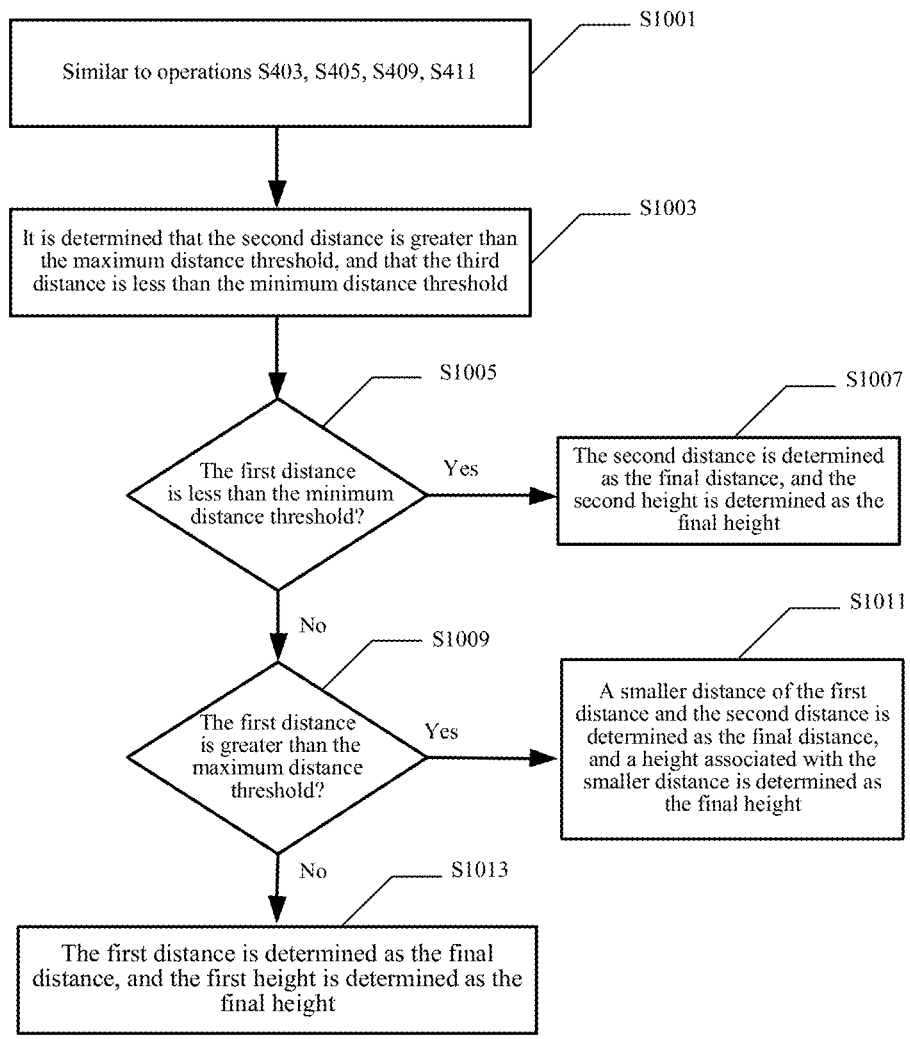
FIG. 10 schematically shows an exemplary flowchart of a seventh example of determining a final distance and a final height according to an embodiment of the present disclosure.

FIG. 10 schematically shows an exemplary flowchart of a seventh example of determining a final distance and a final height according to an embodiment of the present disclosure.

As shown in FIG. 10, the method includes following operations.

In operation S1001, operations similar to operations S403, S405, S409 and S411 in FIG. 4 are performed.

In operation S1003, it is determined that the second distance is greater than the maximum distance threshold, and that the third distance is less than the minimum distance threshold.

In operation S1005, operations similar to operation S401 in FIG. 4 are performed.

In response to a result of "Yes" determined in operation S1005, the process proceeds to operation S1007.

In operation S1007, the second distance is determined as the final distance, and the second height is determined as the final height.

In operation S1009, operations similar to operation S407 in FIG. 4 are performed.

In response to a result of "Yes" determined in operation S1009, the process proceeds to operation S1011.

In operation S1011, a smaller distance of the first distance and the second distance is determined as the final distance, and a height associated with the smaller distance is determined as the final height.

In response to a result of "No" determined in operation S1009, the process proceeds to operation S1013.

In operation S1013, the first distance is determined as the final distance, and the first height is determined as the final height.

Figure 11:
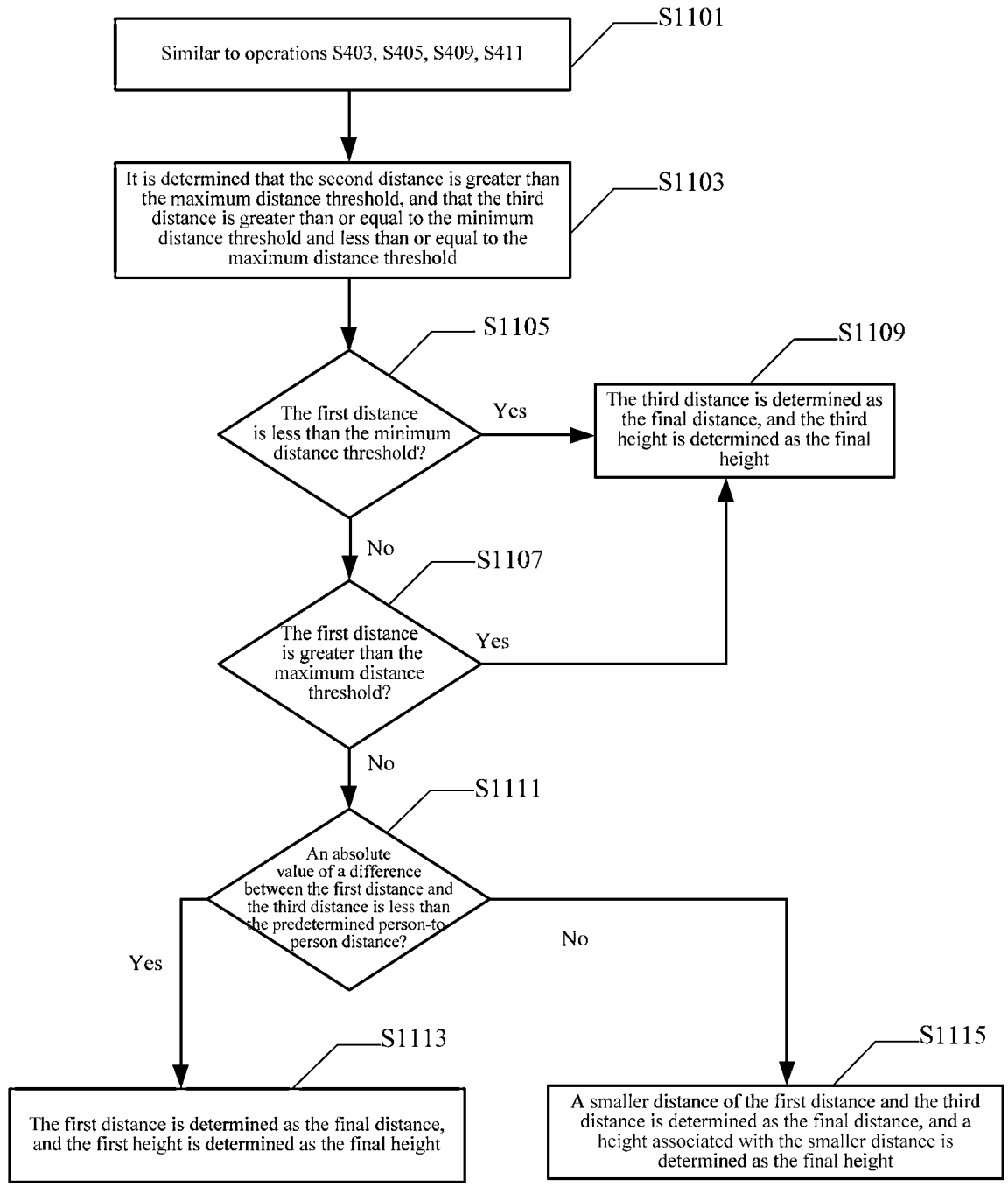
FIG. 11 schematically shows an exemplary flowchart of an eighth example of determining a final distance and a final height according to an embodiment of the present disclosure.

FIG. 11 schematically shows an exemplary flowchart of an eighth example of determining a final distance and a final height according to an embodiment of the present disclosure.

As shown in FIG. 11, the method includes following operations.

In operation S1101, operations similar to operations S403, S405, S409 and S411 in FIG. 4 are performed.

In operation S1103, it is determined that the second distance is greater than the maximum distance threshold, and that the third distance is greater than or equal to the minimum distance threshold and less than or equal to the maximum distance threshold.

In operations S1105 and S1107, operations similar to operations S401 and S407 in FIG. 4 are performed.

In response to a result of "Yes" determined in operation S1105, or in response to a result of "Yes" determined in operation S1107, the process proceeds to operation S1109.

In operation S1109, the third distance is determined as the final distance, and the third height is determined as the final height.

In response to a result of "No" determined in operation S1107, the process proceeds to operation S1111.

In operation S1111, it is determined whether |Da−Dc| is less than PTPD or not.

In response to determining that |Da−Dc| is less than PTPD, the process proceeds to operation S1113, in which the first distance is determined as the final distance, and the first height is determined as the final height.

In response to determining that |Da−Dc| is greater than or equal to PTPD, the process proceeds to operation S1115, in which a smaller distance of the first distance and the third distance is determined as the final distance, and a height associated with the smaller distance is determined as the final height.

Figure 12:
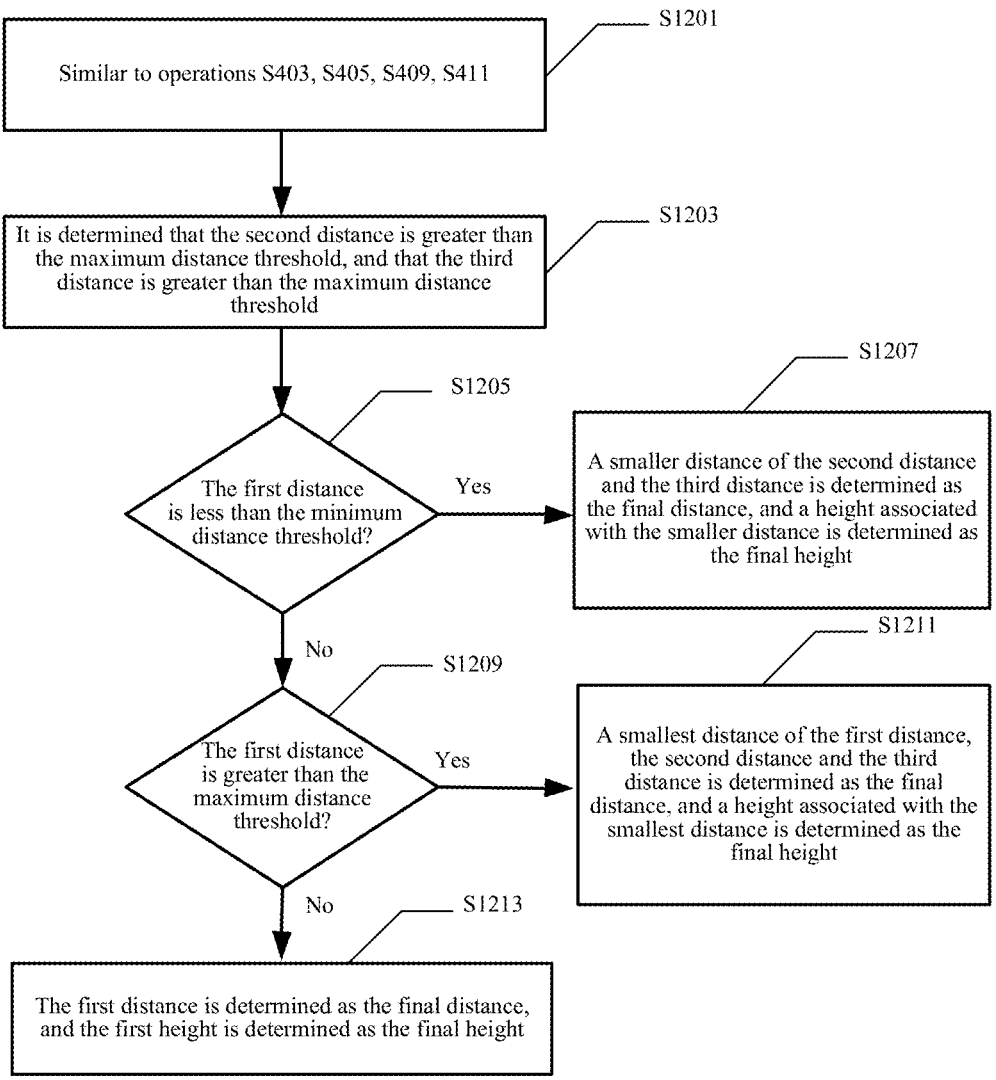
FIG. 12 schematically shows an exemplary flowchart of a ninth example of determining a final distance and a final height according to an embodiment of the present disclosure.

FIG. 12 schematically shows an exemplary flowchart of a ninth example of determining a final distance and a final height according to an embodiment of the present disclosure.

As shown in FIG. 12, the method includes following operations.

In operation S1201, operations similar to operations S403, S405, S409 and S411 in FIG. 4 are performed.

In operation S1203, it is determined that the second distance is greater than the maximum distance threshold, and that the third distance is greater than the maximum distance threshold.

In operation S1205, operations similar to operation S401 in FIG. 4 are performed.

In response to a result of "Yes" determined in operation S1205, the process proceeds to operation S1207.

In operation S1207, a smaller distance of the second distance and the third distance is determined as the final distance, and a height associated with the smaller distance is determined as the final height.

In operation S1209, operations similar to operation S401 in FIG. 4 are performed.

In response to a result of "Yes" determined in operation S1209, the process proceeds to operation S1211.

In operation S1211, a smallest distance of the first distance, the second distance and the third distance is determined as the final distance, and a height associated with the smallest distance is determined as the final height.

In response to a result of "No" determined in operation S1209, the process proceeds to operation S1213.

In operation S1213, the first distance is determined as the final distance, and the first height is determined as the final height.

Figure 13:
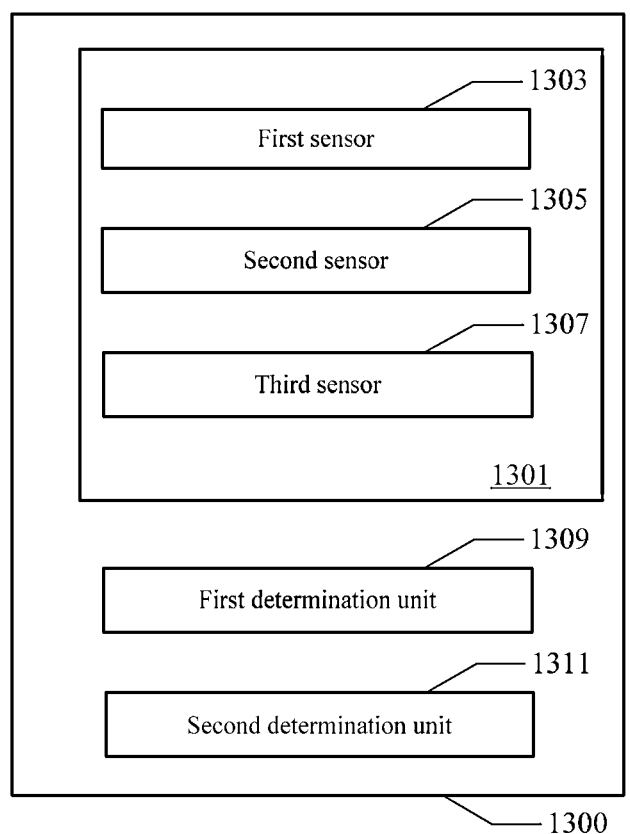
FIG. 13 schematically shows a block diagram of a device of determining a distance and a height based on a plurality of sensors according to an embodiment of the present disclosure, and FIG. 14 schematically shows a block diagram of an electronic apparatus suitable for implementing the method described above according to an embodiment of the present disclosure.

FIG. 13 schematically shows a block diagram of a device of determining a distance and a height based on a plurality of sensors according to an embodiment of the present disclosure.

As shown in FIG. 13, a device 300 of determining a distance and a height based on a plurality of sensors may include a security inspection device 1301, a first determination unit 1309, and a second determination unit 1311. The security inspection device 1301 may include a first sensor 1303, a second sensor 1305 and a third sensor 1307.

The first sensor, the second sensor and the third sensor arranged on the security inspection device may be configured to respectively measure a first distance, a second distance and a third distance from the security inspection device to the tested person as well as measure a first height, a second height and a third height of the tested person.

The first determination unit may be configured to determine a relationship between the first distance and a minimum distance threshold as well as a maximum distance threshold, a relationship between the second distance and the minimum distance threshold as well as the maximum distance threshold, and a relationship between the third distance and the minimum distance threshold as well as the maximum distance threshold.

The second determination unit may be configured to determine a final distance from the security inspection device to the tested person and a final height of the tested person based on the relationships, and perform a pixel conversion and a size conversion on the pupil image of the tested person based on the final distance and the final height, so as to determine whether the tested person takes drugs or not.

In addition to the modules 1301 to 1309, the device of determining the distance and the height based on the plurality of sensors may further include other modules for accordingly executing the operations described above.

For the sake of clarity and conciseness, the various modules and the corresponding operations executed therein will not be repeated here.

The functions of the plurality of modules according to the embodiments of the present disclosure may be implemented in one module. Any module according to the embodiments of the present disclosure may be split into multiple modules for implementation. Any module according to the embodiments of the present disclosure may be implemented at least partially as a hardware circuit, such as a field programmable gate array (FPGA), a programmable logic array (PLA), a system on a chip, a system on a substrate, a system on a package, an Application Specific Integrated Circuit (ASIC), or may be implemented by hardware or firmware in any other reasonable way of integrating or encapsulating the circuit, or may be implemented by any one of the three implementation modes of software, hardware and firmware or an appropriate combination thereof. Alternatively, any module according to the embodiments of the present disclosure may be at least partially implemented as a computer program module that, when executed, perform the corresponding functions.

Any module according to the embodiments of the present disclosure may be implemented at least partially as a hardware circuit, such as a field programmable gate array (FPGA), a programmable logic array (PLA), a system on a chip, a system on a substrate, a system on a package, an Application Specific Integrated Circuit (ASIC), or may be implemented by hardware or firmware in any other reasonable way of integrating or encapsulating the circuit, or may be implemented by any one of the three implementation modes of software, hardware and firmware or an appropriate combination thereof. Alternatively, at least one of the modules described above may be at least partially implemented as a computer program module that, when executed, may perform the corresponding functions.

Figure 14:
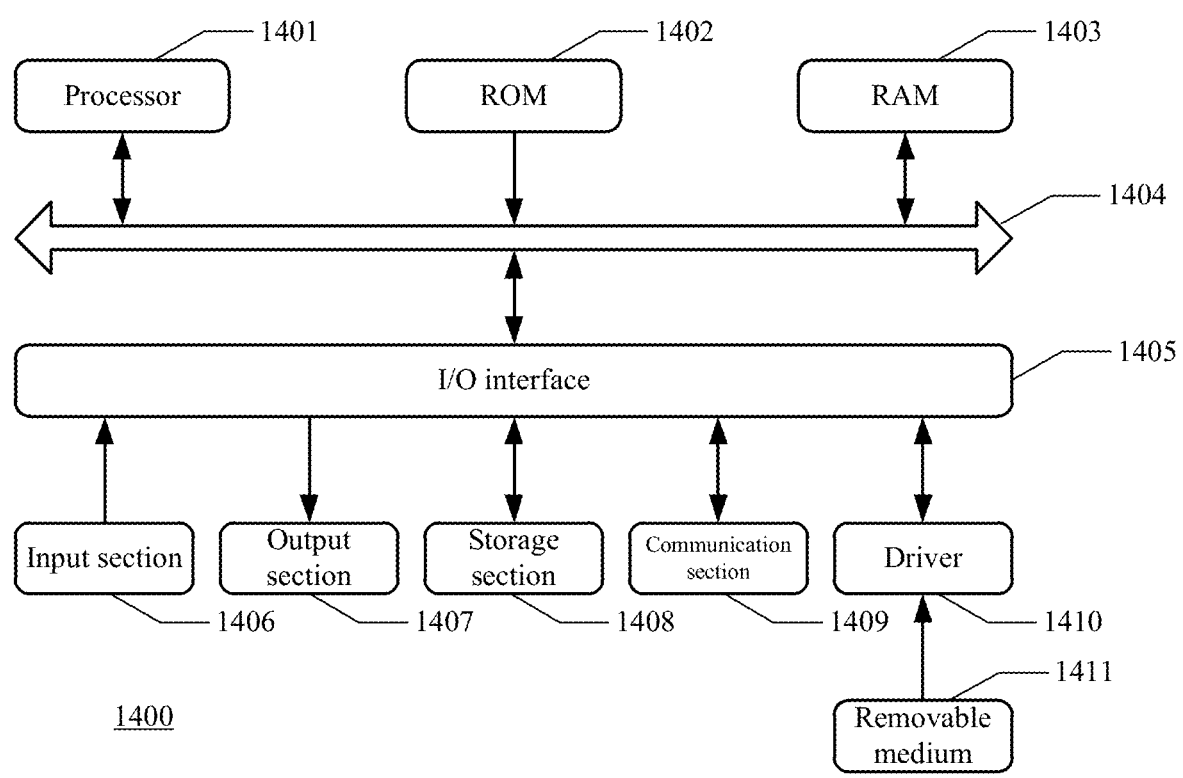

FIG. 14 schematically shows a block diagram of an electronic apparatus suitable for implementing the method described above according to an embodiment of the present disclosure. The electronic apparatus shown in FIG. 14 is only an example, and should not bring any limitation to the function and scope of use of the embodiments of the present disclosure.

As shown in FIG. 14, a computer apparatus 1400 according to the embodiment of the present disclosure includes a processor 1401, which may execute various appropriate actions and processing according to the program stored in a read only memory (ROM) 1402 or the program loaded into a random access memory (RAM) 1403 from a storage section 1408. The processor 1401 may, for example, include a general-purpose microprocessor (for example, CPU), an instruction set processor and/or a related chipset and/or a special-purpose microprocessor (for example, an application specific integrated circuit (ASIC)), and the like. The processor 1401 may also include an on-board memory for caching purposes. The processor 1401 may include a single processing unit or multiple processing units for executing different actions of the method flow according to the embodiments of the present disclosure.

Various programs and data required for the operation of the electronic apparatus 1400 are stored in the RAM 1403. The processor 1401, the ROM 1402 and the RAM 1403 are connected to each other through a bus 1404. The processor 1401 executes various operations of the method flow according to the embodiments of the present disclosure by executing the programs in the ROM 1402 and/or the RAM 1403. It should be noted that the program may also be stored in one or more memories other than the ROM 1402 and the RAM 1403. The processor 1401 may also execute various operations of the method flow according to the embodiments of the present disclosure by executing the programs stored in the one or more memories.

According to the embodiments of the present disclosure, the electronic apparatus 1400 may further include an input/output (I/O) interface 1405 which is also connected to the bus 1404. The electronic apparatus 1400 may further include one or more of the following components connected to the I/O interface 1405: an input section 1406 including a keyboard, a mouse, etc.; an output section 1407 including a cathode ray tube (CRT), a liquid crystal display (LCD), etc. and a speaker, etc.; a storage section 1408 including a hard disk, etc.; and a communication section 1409 including a network interface card such as a LAN card, a modem, and the like. The communication section 1409 performs communication processing via a network such as the Internet. A drive 810 is also connected to the I/O interface 1405 as required. A removable medium 811, such as a magnetic disk, an optical disk, a magneto-optical disk, a semiconductor memory, and the like, is installed on the drive 810 as required, so that the computer program read therefrom is installed into the storage section 1408 as needed.

The method flow according to the embodiments of the present disclosure may be implemented as a computer software program. For example, the embodiments of the present disclosure include a computer program product including a computer program carried on a computer-readable storage medium. The computer program includes a program code for execution of the method shown in the flowchart. In such an embodiment, the computer program may be downloaded and installed from the network through the communication section 1409, and/or installed from the removable medium 811. When the computer program is executed by the processor 1401, the above-mentioned functions defined in the system of the embodiment of the present disclosure are performed. According to the embodiments of the present disclosure, the above-described systems, apparatuses, devices, modules, units, etc. may be implemented by computer program modules.

The present disclosure also provides a computer-readable storage medium, which may be included in the apparatus/device/system described in the above embodiments; or exist alone without being assembled into the apparatus/device/system. The above-mentioned computer-readable storage medium carries one or more programs that when executed, perform the method according to the embodiments of the present disclosure.

According to the embodiments of the present disclosure, the computer-readable storage medium may be a non-volatile computer-readable storage medium, for example, may include but not limited to: portable computer disk, hard disk, random access memory (RAM), read-only memory (ROM), erasable programmable read-only memory (EPROM or flash memory), portable compact disk read-only memory (CD-ROM), optical storage device, magnetic storage device, or any suitable combination of the above. In the present disclosure, the computer-readable storage medium may be any tangible medium that includes or stores programs that may be used by or in combination with an instruction execution system, apparatus, or device. For example, according to the embodiments of the present disclosure, the computer-readable storage medium may include the ROM 1402 and/or the RAM 1403 described above and/or one or more memories other than the ROM 1402 and the RAM 1403.

The flowcharts and block diagrams in the accompanying drawings illustrate the possible architecture, functions, and operations of the system, method, and computer program product according to various embodiments of the present disclosure. In this regard, each block in the flowcharts or block diagrams may represent a part of a module, program segment, or code, which part includes one or more executable instructions for implementing the specified logical function. It should also be noted that, in some alternative implementations, the functions noted in the blocks may also occur in a different order than that noted in the accompanying drawings. For example, two blocks shown in succession may actually be executed substantially in parallel, or they may sometimes be executed in the reverse order, depending on the functions involved. It should also be noted that each block in the block diagrams or flowcharts, and the combination of blocks in the block diagrams or flowcharts, may be implemented by a dedicated hardware-based system that performs the specified functions or operations, or may be implemented by a combination of dedicated hardware and computer instructions.

Those skilled in the art may understand that the various embodiments of the present disclosure and/or the features described in the claims may be combined in various ways, even if such combinations are not explicitly described in the present disclosure. In particular, without departing from the spirit and teachings of the present disclosure, the various embodiments of the present disclosure and/or the features described in the claims may be combined in various ways. All these combinations fall within the scope of the present disclosure.

The embodiments of the present disclosure have been described above. However, these embodiments are for illustrative purposes only, and are not intended to limit the scope of the present disclosure. Although the embodiments have been described separately above, this does not mean that measures in the respective embodiments may not be used in combination advantageously. The scope of the present disclosure is defined by the appended claims and their equivalents. Without departing from the scope of the present disclosure, those skilled in the art may make various substitutions and modifications, and these substitutions and modifications should all fall within the scope of the present disclosure.

What is claimed is:

1. A method of determining a distance and a height by using a plurality of sensors so as to determine whether a tested person takes drugs or not based on a pupil image of the tested person, comprising:

measuring, by respectively using a first sensor, a second sensor and a third sensor of the plurality of sensors arranged on a security inspection device, a first distance, a second distance and a third distance from the security inspection device to the tested person as well as measuring a first height, a second height and a third height of the tested person;

determining, by using a first determination unit, a relationship between the first distance and a minimum distance threshold as well as a maximum distance threshold, a relationship between the second distance and the minimum distance threshold as well as the maximum distance threshold, and a relationship between the third distance and the minimum distance threshold as well as the maximum distance threshold;

determining, by using a second determination unit, a final distance from the security inspection device to the tested person and a final height of the tested person, based on the relationships; and performing a pixel conversion and a size conversion on the pupil image of the tested person based on the final distance and the final height, so as to determine whether the tested person takes drugs or not, wherein the determining a final distance from the security inspection device to the tested person and a final height of the tested person, based on the relationships comprises:

determining the first distance as the final distance from the security inspection device to the tested person and determining the first height as the final height of the tested person in response to determining that the second distance is less than the minimum distance threshold and the third distance is less than the minimum distance threshold, regardless of the relationship between the first distance and the minimum distance threshold as well as the maximum distance threshold.

2. The method of determining a distance and a height by using a plurality of sensors of claim 1, wherein the determining a final distance from the security inspection device to the tested person and a final height of the tested person, based on the relationships comprises:

in response to determining that the second distance is less than the minimum distance threshold, and that the third distance is greater than or equal to the minimum distance threshold and less than or equal to the maximum distance threshold, determining the third distance as the final distance from the security inspection device to the tested person and determining the third height as the final height of the tested person, in response to determining that the first distance is less than the minimum distance threshold or greater than the maximum distance threshold; or determining whether an absolute value of a difference between the first distance and the third distance is less than a predetermined person-to-person distance or not, in response to determining that the first distance is greater than or equal to the minimum distance threshold and less than or equal to the maximum distance threshold, determining the first distance as the final distance from the security inspection device to the tested person and determining the first height as the final height of the tested person, in response to determining that the absolute value of the difference between the first distance and the third distance is less than the predetermined person-to-person distance; and determining a smaller distance of the first distance and the third distance as the final distance from the security inspection device to the tested person and determining a height associated with the smaller distance as the final height of the tested person, in response to determining that the absolute value of the difference between the first distance and the third distance is greater than or equal to the predetermined person-to-person distance.

3. The method of determining a distance and a height by using a plurality of sensors of claim 1, wherein the determining a final distance from the security inspection device to the tested person and a final height of the tested person, based on the relationships comprises:

in response to determining that the second distance is less than the minimum distance threshold and that the third distance is greater than the maximum distance threshold, determining the third distance as the final distance from the security inspection device to the tested person and determining the third height as the final height of the tested person, in response to determining that the first distance is less than the minimum distance threshold; or determining a smaller distance of the first distance and the third distance as the final distance from the security inspection device to the tested person and determining a height associated with the smaller distance as the final height of the tested person, in response to determining that the first distance is greater than the maximum distance threshold; or determining the first distance as the final distance from the security inspection device to the tested person and determining the first height as the final height of the tested person, in response to determining that the first distance is greater than or equal to the minimum distance threshold and less than or equal to the maximum distance threshold.

4. The method of determining a distance and a height by using a plurality of sensors of claim 1, wherein the determining a final distance from the security inspection device to the tested person and a final height of the tested person, based on the relationships comprises:

in response to determining that the second distance is greater than the minimum distance threshold and less than the maximum distance threshold, and that the third distance is less than the maximum distance threshold, determining the second distance as the final distance from the security inspection device to the tested person and determining the second height as the final height of the tested person, in response to determining that the first distance is less than the minimum distance threshold or greater than the maximum distance threshold; or determining whether an absolute value of a difference between the first distance and the second distance is less than a predetermined person-to-person distance or not, in response to determining that the first distance is greater than the minimum distance threshold and less than the maximum distance threshold, determining the first distance as the final distance from the security inspection device to the tested person and determining the first height as the final height of the tested person, in response to determining that the absolute value of the difference between the first distance and the second distance is less than the predetermined person-to-person distance; and determining a smaller distance of the first distance and the second distance as the final distance from the security inspection device to the tested person and determining a height associated with the smaller distance as the final height of the tested person, in response to determining that the absolute value of the difference between the first distance and the second distance is greater than or equal to the predetermined person-to-person distance.

5. The method of determining a distance and a height by using a plurality of sensors of claim 1, wherein the determining a final distance from the security inspection device to the tested person and a final height of the tested person, based on the relationships comprises:

in response to determining that the second distance is greater than or equal to the minimum distance threshold and less than or equal to the maximum distance threshold, and that the third distance is greater than or equal to the minimum distance threshold and less than or equal to the maximum distance threshold, determining whether an absolute value of a difference between the second distance and the third distance is less than a predetermined person-to-person distance or not, in response to determining that the first distance is less than the minimum distance threshold or greater than the maximum distance threshold, determining the second distance as the final distance from the security inspection device to the tested person and determining the second height as the final height of the tested person, in response to determining that the absolute value of the difference between the second distance and the third distance is less than the predetermined person-to-person distance; and determining a smaller distance of the second distance and the third distance as the final distance from the security inspection device to the tested person and determining a height associated with the smaller distance as the final height of the tested person, in response to determining that the absolute value of the difference between the second distance and the third distance is greater than or equal to the predetermined person-to-person distance; or determining whether an absolute value of a difference between the first distance and the second distance is less than a predetermined person-to-person distance or not, whether an absolute value of a difference between the first distance and the third distance is less than the predetermined person-to-person distance or not, and whether an absolute value of a difference between the second distance and the third distance is less than the predetermined person-to-person distance or not, in response to determining that the first distance is greater than or equal to the minimum distance threshold and less than or equal to the maximum distance threshold,
  determining the first distance as the final distance from the security inspection device to the tested person and determining the first height as the final height of the tested person, in response to determining that the absolute value of the difference between the first distance and the second distance is less than the predetermined person-to-person distance, the absolute value of the difference between the first distance and the third distance is less than the predetermined person-to-person distance, and the absolute value of the difference between the second distance and the third distance is less than the predetermined person-to-person distance; or
  determining the third distance as the final distance from the security inspection device to the tested person and determining the third height as the final height of the tested person, in response to determining that the absolute value of the difference between the first distance and the second distance is greater than or equal to the predetermined person-to-person distance, the absolute value of the difference between the first distance and the third distance is less than the predetermined person-to-person distance, and the absolute value of the difference between the second distance and the third distance is less than the predetermined person-to-person distance; or
  determining the first distance as the final distance from the security inspection device to the tested person and determining the first height as the final height of the tested person, in response to determining that the absolute value of the difference between the first distance and the second distance is less than the predetermined person-to-person distance, the absolute value of the difference between the first distance and the third distance is less than the predetermined person-to-person distance, and the absolute value of the difference between the second distance and the third distance is greater than or equal to the predetermined person-to-person distance; or
  determining the second distance as the final distance from the security inspection device to the tested person and determining the second height as the final height of the tested person, in response to determining that the absolute value of the difference between the first distance and the second distance is less than the predetermined person-to-person distance, the absolute value of the difference between the second distance and the third distance is less than the predetermined person-to-person distance, and the absolute value of the difference between the first distance and the third distance is greater than or equal to the predetermined person-to-person distance; or
  determining the third distance as the final distance from the security inspection device to the tested person and determining the third height as the final height of the tested person, in response to determining that the absolute value of the difference between the first distance and the second distance is less than the predetermined person-to-person distance, the absolute value of the difference between the first distance and the third distance is greater than or equal to the predetermined person-to-person distance, and the absolute value of the difference between the second distance and the third distance is greater than or equal to the predetermined person-to-person distance; or
  determining the second distance as the final distance from the security inspection device to the tested person and determining the second height as the final height of the tested person, in response to determining that the absolute value of the difference between the first distance and the second distance is greater than or equal to the predetermined person-to-person distance, the absolute value of the difference between the first distance and the third distance is greater than or equal to the predetermined person-to-person distance, and the absolute value of the difference between the second distance and the third distance is less than the predetermined person-to-person distance; or
  determining the first distance as the final distance from the security inspection device to the tested person and determining the first height as the final height of the tested person, in response to determining that the absolute value of the difference between the first distance and the second distance is greater than or equal to the predetermined person-to-person distance, the absolute value of the difference between the second distance and the third distance is greater than or equal to the predetermined person-to-person distance, and the absolute value of the difference between the first distance and the third distance is less than the predetermined person-to-person distance; or
  determining the third distance as the final distance from the security inspection device to the tested person and determining the third height as the final height of the tested person, in response to determining that the absolute value of the difference between the first distance and the second distance is greater than or equal to the predetermined person-to-person distance, the absolute value of the difference between the first distance and the third distance is greater than or equal to the predetermined person-to-person distance, and the absolute value of the difference between the second distance and the third distance is greater than or equal to the predetermined person-to-person distance.

6. The method of determining a distance and a height by using a plurality of sensors of claim 1, wherein the determining a final distance from the security inspection device to the tested person and a final height of the tested person, based on the relationships comprises:
  in response to determining that the second distance is greater than or equal to the minimum distance threshold and less than or equal to the maximum distance threshold, and that the third distance is greater than the maximum distance threshold,
  determining the second distance as the final distance from the security inspection device to the tested person and determining the second height as the final height of the tested person, in response to determining that the first distance is less than the minimum distance threshold or greater than the maximum distance threshold; or
  determining whether an absolute value of a difference between the first distance and the second distance is less than a predetermined person-to-person distance or not, in response to determining that the first distance is greater than or equal to the minimum distance threshold and less than or equal to the maximum distance threshold,
    determining the first distance as the final distance from the security inspection device to the tested person and determining the first height as the final height of the tested person, in response to determining that the absolute value of the difference between the first distance and the second distance is less than the predetermined person-to-person distance; or
    determining a smaller distance of the first distance and the second distance as the final distance from the security inspection device to the tested person and determining a height associated with the smaller distance as the final height of the tested person, in response to determining that the absolute value of the difference between the first distance and the second distance is greater than or equal to the predetermined person-to-person distance.

7. The method of determining a distance and a height by using a plurality of sensors of claim 1, wherein the determining a final distance from the security inspection device to the tested person and a final height of the tested person, based on the relationships comprises:
  in response to determining that the second distance is greater than the maximum distance threshold, and that the third distance is less than the minimum distance threshold,
    determining the second distance as the final distance from the security inspection device to the tested person and determining the second height as the final height of the tested person, in response to determining that the first distance is less than the minimum distance threshold; or
    determining a smaller distance of the first distance and the second distance as the final distance from the security inspection device to the tested person and determining a height associated with the smaller distance as the final height of the tested person, in response to determining that the first distance is greater than the maximum distance threshold; or
  determining the first distance as the final distance from the security inspection device to the tested person and determining the first height as the final height of the tested person, in response to determining that the first distance is greater than or equal to the minimum distance threshold and less than or equal to the maximum distance threshold.

8. The method of determining a distance and a height by using a plurality of sensors of claim 1, wherein the determining a final distance from the security inspection device to the tested person and a final height of the tested person, based on the relationships comprises:
  in response to determining that the second distance is greater than the maximum distance threshold, and that the third distance is greater than or equal to the minimum distance threshold and less than or equal to the maximum distance threshold,
    determining the third distance as the final distance from the security inspection device to the tested person and determining the third height as the final height of the tested person, in response to determining that the first distance is less than the minimum distance threshold or greater than the maximum distance threshold; or
    determining whether an absolute value of a difference between the first distance and the third distance is less than a predetermined person-to-person distance or not, in response to determining that the first distance is greater than or equal to the minimum distance threshold and less than or equal to the maximum distance threshold,
      determining the first distance as the final distance from the security inspection device to the tested person and determining the first height as the final height of the tested person, in response to determining that the absolute value of the difference between the first distance and the third distance is less than the predetermined person-to-person distance; or
      determining a smaller distance of the first distance and the third distance as the final distance from the security inspection device to the tested person and determining a height associated with the smaller distance as the final height of the tested person, in response to determining that the absolute value of the difference between the first distance and the third distance is greater than or equal to the predetermined person-to-person distance.

9. The method of determining a distance and a height by using a plurality of sensors of claim 1, wherein the determining a final distance from the security inspection device to the tested person and a final height of the tested person, based on the relationships comprises:
  in response to determining that the second distance is greater than the maximum distance threshold, and the third distance is greater than the maximum distance threshold,
    determining a smaller distance of the second distance and the third distance as the final distance from the security inspection device to the tested person and determining a height associated with the smaller distance as the final height of the tested person, in response to determining that the first distance is less than the minimum distance threshold; or
    determining a smallest distance of the first distance, the second distance and the third distance as the final distance from the security inspection device to the tested person and determining a height associated with the smallest distance as the final height of the tested person, in response to determining that the first distance is greater than the maximum distance threshold; or
    determining the first distance as the final distance from the security inspection device to the tested person and determining the first height as the final height of the tested person, in response to determining that the first distance is greater than or equal to the minimum distance threshold and less than or equal to the maximum distance threshold.

10. A device of determining a distance and a height by using a plurality of sensors so as to determine whether a tested person takes drugs or not based on a pupil image of the tested person, comprising:
- a first sensor, a second sensor and a third sensor of the plurality of sensors arranged on a security inspection device, configured to respectively measure a first distance, a second distance and a third distance from the security inspection device to the tested person as well as measure a first height, a second height and a third height of the tested person;
- a first determination unit, configured to determine a relationship between the first distance and a minimum distance threshold as well as a maximum distance threshold, a relationship between the second distance and the minimum distance threshold as well as the maximum distance threshold, and a relationship between the third distance and the minimum distance threshold as well as the maximum distance threshold; and
- a second determination unit, configured to:
  - determine a final distance from the security inspection device to the tested person and a final height of the tested person, based on the relationships;
  - perform a pixel conversion and a size conversion on the pupil image of the tested person based on the final distance and the final height, so as to determine whether the tested person takes drugs or not; and
  - determine the first distance as the final distance from the security inspection device to the tested person and determine the first height as the final height of the tested person, in response to determining that the second distance is less than the minimum distance threshold and the third distances is less than the minimum distance threshold, regardless of the relationship between the first distance and the minimum distance threshold as well as the maximum distance threshold.

11. An electronic apparatus, comprising:
one or more processors; and
a memory for storing one or more computer programs,
wherein the one or more programs, when executed by the one or more processors, cause the one or more processors to perform the method of claim 1.

12. A computer-readable storage medium having executable instructions stored thereon that, when executed by a processor, cause the processor to perform the method of claim 1.

* * * * *